United States Patent
Lemoine

(10) Patent No.: US 8,636,737 B2
(45) Date of Patent: Jan. 28, 2014

(54) MODULAR OCCIPITAL PLATE

(75) Inventor: Jeremy Lemoine, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 781 days.

(21) Appl. No.: 11/756,106

(22) Filed: May 31, 2007

(65) Prior Publication Data

US 2008/0177314 A1      Jul. 24, 2008

Related U.S. Application Data

(63) Continuation-in-part of application No. 11/616,720, filed on Dec. 27, 2006, now Pat. No. 8,246,662.

(51) Int. Cl.
- *A61B 17/80* (2006.01)
- *A61B 17/84* (2006.01)
- *A61B 17/88* (2006.01)
- *A61B 17/70* (2006.01)

(52) U.S. Cl.
USPC ............. 606/71; 606/281; 606/252; 606/286; 606/269

(58) Field of Classification Search
USPC ...................... 606/280–299, 70–71, 250–253
See application file for complete search history.

(56) References Cited

U.S. PATENT DOCUMENTS

| | | |
|---|---|---|
| 4,763,644 A | 8/1988 | Webb |
| 4,805,602 A | 2/1989 | Puno et al. |
| 4,836,193 A | 6/1989 | Ransford |
| 4,841,959 A | 6/1989 | Ransford |
| 4,887,596 A | 12/1989 | Sherman |
| 4,950,269 A | 8/1990 | Gaines, Jr. |
| 5,129,388 A | 7/1992 | Vignaud et al. |
| 5,360,429 A | 11/1994 | Jeanson et al. |
| 5,498,264 A | 3/1996 | Schlapfer et al. |
| 5,507,745 A | 4/1996 | Logroscino et al. |
| 5,520,689 A | 5/1996 | Schlapfer et al. |
| 5,531,745 A | 7/1996 | Ray |
| 5,542,946 A | 8/1996 | Logroscino et al. |
| 5,545,164 A | 8/1996 | Howland |

(Continued)

FOREIGN PATENT DOCUMENTS

| | | |
|---|---|---|
| EP | 0737449 A1 | 10/1996 |
| EP | 1 180 348 A2 | 2/2002 |

(Continued)

OTHER PUBLICATIONS

Office Action issued in U.S. Appl. No. 11/085,672 mailed Nov. 17, 2006, Piehl, 9 pages.

(Continued)

*Primary Examiner* — Michael T Schaper

(74) *Attorney, Agent, or Firm* — Seager, Tufte & Wickhem, LLC

(57) ABSTRACT

A system and associated method are provided for mechanically fixating a region of a skull to a portion of a spine. A plate is provided to contact a region of a skull and be secured thereto. A spinal rod is configured to extend from a location adjacent the plate to a location adjacent at least one vertebra. An adjustable housing is provided to secure the rod to the plate, and has a first position wherein the relative position of the rod to the plate can be adjusted and a second position wherein the relative position of the rod to the plate is secured.

14 Claims, 28 Drawing Sheets

(56) References Cited

U.S. PATENT DOCUMENTS

| | | | |
|---|---|---|---|
| 5,558,674 | A | 9/1996 | Heggeness et al. |
| 5,653,708 | A | 8/1997 | Howland |
| 5,665,089 | A | 9/1997 | Dall |
| 5,707,372 | A | 1/1998 | Errico et al. |
| 5,713,898 | A | 2/1998 | Stucker et al. |
| 5,928,233 | A | 7/1999 | Apfelbaum et al. |
| 5,976,135 | A | 11/1999 | Sherman et al. |
| 6,017,343 | A | 1/2000 | Rogozinski |
| 6,077,262 | A | 6/2000 | Schlapfer et al. |
| 6,096,040 | A | 8/2000 | Esser |
| 6,146,382 | A | 11/2000 | Hurlbert |
| 6,187,005 | B1 | 2/2001 | Brace et al. |
| 6,206,882 | B1 | 3/2001 | Cohen |
| 6,238,396 | B1 | 5/2001 | Lombardo |
| 6,296,644 | B1 | 10/2001 | Saurat et al. |
| 6,302,883 | B1 | 10/2001 | Bono |
| 6,315,779 | B1 | 11/2001 | Morrison |
| 6,336,927 | B2 | 1/2002 | Rogozinski |
| 6,368,351 | B1 | 4/2002 | Glenn et al. |
| 6,379,358 | B1 | 4/2002 | Kuo |
| 6,432,109 | B1 | 8/2002 | Letendart et al. |
| 6,485,491 | B1 | 11/2002 | Farris et al. |
| 6,524,315 | B1 | 2/2003 | Selvitelli et al. |
| 6,547,790 | B2 | 4/2003 | Harkey, III et al. |
| 6,620,164 | B2 | 9/2003 | Ueyama et al. |
| 6,682,532 | B2 | 1/2004 | Johnson |
| 6,832,999 | B2 | 12/2004 | Ueyama et al. |
| 6,902,565 | B2 | 6/2005 | Berger et al. |
| 6,949,123 | B2 | 9/2005 | Reiley |
| 6,958,065 | B2 | 10/2005 | Ueyama et al. |
| 7,033,377 | B2 | 4/2006 | Miller |
| 7,060,069 | B2 | 6/2006 | Kozak et al. |
| 7,232,441 | B2 | 6/2007 | Altarac et al. |
| 7,250,052 | B2 | 7/2007 | Landry et al. |
| 7,303,563 | B2 | 12/2007 | Poyner et al. |
| 7,491,218 | B2 | 2/2009 | Landry et al. |
| 7,618,443 | B2 | 11/2009 | Abdou |
| 7,621,942 | B2 | 11/2009 | Piehl |
| 7,857,836 | B2 * | 12/2010 | Huebner et al. ............... 606/280 |
| 7,901,433 | B2 | 3/2011 | Forton et al. |
| 2002/0049446 | A1 | 4/2002 | Harkey, III |
| 2002/0120268 | A1 | 8/2002 | Berger |
| 2003/0004512 | A1 | 1/2003 | Farris et al. |
| 2003/0036759 | A1 | 2/2003 | Musso |
| 2003/0153913 | A1 | 8/2003 | Altarac et al. |
| 2003/0163132 | A1 | 8/2003 | Chin |
| 2003/0176863 | A1 | 9/2003 | Ueyama et al. |
| 2004/0068319 | A1 * | 4/2004 | Cordaro .................... 623/17.11 |
| 2004/0122426 | A1 | 6/2004 | Michelson |
| 2004/0127904 | A1 | 7/2004 | Kinieczynski et al. |
| 2004/0153070 | A1 | 8/2004 | Barker et al. |
| 2004/0172022 | A1 | 9/2004 | Landry et al. |
| 2004/0267259 | A1 | 12/2004 | Mazda et al. |
| 2005/0010227 | A1 | 1/2005 | Paul |
| 2005/0080417 | A1 | 4/2005 | Alexis et al. |
| 2005/0119656 | A1 | 6/2005 | Ferrante et al. |
| 2005/0124994 | A1 | 6/2005 | Berger et al. |
| 2005/0216005 | A1 | 9/2005 | Howland |
| 2005/0216008 | A1 | 9/2005 | Zwirnmann |
| 2005/0228382 | A1 | 10/2005 | Richelsoph et al. |
| 2005/0240185 | A1 | 10/2005 | Boomer et al. |
| 2005/0251141 | A1 | 11/2005 | Frigg et al. |
| 2005/0273104 | A1 | 12/2005 | Oepen et al. |
| 2005/0277939 | A1 | 12/2005 | Miller |
| 2005/0283153 | A1 * | 12/2005 | Poyner et al. .................. 606/61 |
| 2005/0288669 | A1 | 12/2005 | Abdou |
| 2006/0004359 | A1 | 1/2006 | Kramer et al. |
| 2006/0004360 | A1 | 1/2006 | Kramer et al. |
| 2006/0004363 | A1 | 1/2006 | Brockmeyer et al. |
| 2006/0155283 | A1 | 7/2006 | Doherty et al. |
| 2006/0155284 | A1 | 7/2006 | Doherty et al. |
| 2006/0184170 | A1 | 8/2006 | Kapitan et al. |
| 2006/0217710 | A1 | 9/2006 | Abdou |
| 2006/0217723 | A1 | 9/2006 | Suh |
| 2006/0217724 | A1 * | 9/2006 | Suh et al. ........................ 606/71 |
| 2006/0229610 | A1 | 10/2006 | Piehl |
| 2006/0264932 | A1 | 11/2006 | Bert |
| 2007/0016189 | A1 | 1/2007 | Lake |
| 2007/0083201 | A1 | 4/2007 | Jones et al. |
| 2007/0118121 | A1 | 5/2007 | Purcell et al. |
| 2007/0123872 | A1 | 5/2007 | Brockmeyer et al. |
| 2007/0299441 | A1 | 12/2007 | Hoffman |
| 2008/0051783 | A1 | 2/2008 | Null et al. |
| 2008/0086124 | A1 | 4/2008 | Forton |
| 2008/0125781 | A1 | 5/2008 | Hoffman |
| 2008/0147123 | A1 | 6/2008 | Schermerhorn |
| 2008/0177313 | A1 | 7/2008 | Lemoine |
| 2008/0300635 | A1 | 12/2008 | Lieponis |
| 2009/0270924 | A1 | 10/2009 | Wing et al. |

FOREIGN PATENT DOCUMENTS

| | | |
|---|---|---|
| EP | 1180348 A2 | 2/2002 |
| FR | 2687561 A1 | 2/1992 |
| FR | 2760629 A1 | 3/1997 |
| WO | WO 9531147 A1 | 11/1995 |
| WO | WO 9723170 A1 | 7/1997 |
| WO | WO 9841160 A1 | 9/1998 |
| WO | WO 2005/122922 A2 | 12/2005 |
| WO | WO 2006019370 A1 | 2/2006 |
| WO | WO 2006/096756 A2 | 9/2006 |
| WO | WO 2006102222 A2 | 9/2006 |
| WO | WO 2006102222 A3 | 9/2006 |
| WO | WO 2007044716 A1 | 4/2007 |
| WO | WO 2007146482 A2 | 12/2007 |
| WO | WO 2008042633 A2 | 4/2008 |

OTHER PUBLICATIONS

Interpore Cross International, "Introducing the Altrius OCT System," Biological & Structural Innovation, Interpore Cross Intl, Irvine, CA, Copyright 2003, 2 pages.

Blackstone Medical Inc., "Ascent Posterior Occipital Cervico-Thoracic System," Cervical and Thoracolumbar Systems, www.blackstonemedical.com., Copyright 2005, 1 page.

Globus Medical, Cervical Webpage, Copyright 2005, downloaded from http://www.globusmedical.com/products/cervical.php, on Feb. 2, 2006, 1 page.

Depuy Spine, "Mountaineer OCT Spinal System," Copyright 2006, DePuy Spine, Inc., Raynham, MA, Mar. 2005, 6 pages.

Office Action issued in U.S. Appl. No. 11/085,672 mailed May 18, 2007, Piehl, 15 pages.

Office Action issued in U.S. Appl. No. 11/085,672 mailed Nov. 1, 2007, Piehl, 8 pages.

International Search Report and Written Opinion issued in PCT/US2007/066039, mailed Apr. 14, 2008, Zimmer Spine, Inc., 11 pages.

International Search Report and Written Opinion in PCT/US2007/079295 mailed Apr. 17, 2008, Abbott Laboratories, 14 pages.

Office Action issued in U.S. Appl. No. 11/085,672 mailed Apr. 29, 2008, Piehl, 9 pages.

Office Action issued in U.S. Appl. No. 11/423,201 mailed Sep. 3, 2008, Hoffman, 15 pages.

Office Action issued in U.S. Appl. No. 11/085,672 mailed Oct. 31, 2008, Piehl, 9 pages.

Office Action issued in U.S. Appl. No. 11/423,201 mailed Dec. 10, 2008, Hoffman, 17 pages.

International Preliminary Report on Patentability and Written Opinion issued in PCT/US2007/066039, mailed Dec. 10, 2008, Zimmer Spine, Inc., 6 pages.

Office Action issued in U.S. Appl. No. 11/423,201 mailed Mar. 5, 2009, Hoffman, 15 pages.

Office Action issued in U.S. Appl. No. 11/542,786 mailed Mar. 5, 2009, Forton, 7 pages.

Office Action issued in U.S. Appl. No. 11/085,672 mailed May 7, 2009, Piehl, 12 pages.

Office Action issued in U.S. Appl. No. 11/563,902 mailed May 8, 2009, Hoffman, 9 pages.

International Search Report and Written Opinion issued in PCT/US2006/009996 mailed Jul. 19, 2007, Zimmer Spine, Inc., 10 pages.

(56) References Cited

OTHER PUBLICATIONS

International Preliminary Report on Patentability issued in PCT/US2006/009996, mailed Sep. 25, 2007, Zimmer Spine, Inc., 8 pages.
International Preliminary Report on Patentability and Written Opinion issued in PCT/US2007/079295 mailed Apr. 7, 2009, Abbott Laboratories, 7 pages.
Office Action issued in U.S. Appl. No. 11/616,720 mailed May 27, 2009, Lemoine, 8 pages.
International Preliminary Report on Patentability, Chapter I, and Written Opinion issued in PCT/US2007/085190, mailed Jun. 30, 2009, Abbott Spine Inc., 8 pages.
Office Action issued in U.S. Appl. No. 11/616,720 mailed Dec. 24, 2009, 11 pgs.
International Search Report and Written Opinion, PCT/US2007/085190, mailed Jun. 3, 2008, 13 pages.
Office Action issued in U.S. Appl. No. 11/542,786 mailed Sep. 30, 2009, 8 pgs.
Office Action issued in U.S. Appl. No. 11/563,902 mailed Oct. 27, 2009, 10 pgs.
Office Action issued in U.S. Appl. No. 11/423,201 mailed Oct. 29, 2009, 11 pgs.
International Search Report and Written Opinion, PCT/US2007/085190, mailed Jun. 3, 2008, 13 pgs.
Summit SI OCT Spinal Fixation System, undated, 2 pages; previously cited in U.S. Appl. No. 11/085,672 on Mar. 21, 2005.
Stryker Spine Products, "Products: Cervical OASYS" Webpage, undated, 1 page; previously cited in U.S. Appl. No. 11/085,672 on Mar. 21, 2005.
Blackstone Ascent, Production Information Page, undated, 1 page; previously cited in U.S. Appl. No. 11/085,672 on Mar. 21, 2005.
Globus Medical, Protex CT . . . The new standard in OCT Stabilization systems, www.globusmedical.com, 1-866-456-2871, undated, 1 page; previously cited in U.S. Appl. No. 11/563,902 on Mar. 9, 2007.
Office Action issued in U.S. Appl. No. 11/542,786 mailed Mar. 15, 2010, 9 pgs.
Office Action issued in U.S. Appl. No. 12/609,868 mailed Dec. 8, 2010, 16 pgs.
Office Action issued in U.S. Appl. No. 11/616,720 mailed Jun. 10, 2010, 10 pgs.
Notice of Allowance issued in U.S. Appl. No. 11/542,786 mailed Aug. 26, 2010, 4 pgs.
Examination Report for European Patent Application No. 06738970.0, dated Oct. 21, 2010, European Patent Office, 7 pgs.
Office Action issued in U.S. Appl. No. 11/616,720 mailed Nov. 9, 2010, 11 pgs.
Office Action for U.S. Appl. No. 11/563,902, mailed Jun. 7, 2011, 19 pgs.
Office Action for U.S. Appl. No. 11/563,902 mailed Jan. 31, 2011, 13 pgs.
Notice of Allowance for U.S. Appl. No. 12/609,868, mailed Apr. 14, 2011, 8 pgs.

* cited by examiner

MODULAR OCCIPITAL PLATE

This application is a continuation-in-part of application Ser. No. 11/616,720, filed on Dec. 27, 2006, now U.S. Pat. No. 8,246,662 the contents of which are hereby incorporated by reference.

BACKGROUND OF THE INVENTION

1. Field of the Invention

The present invention relates to spinal fixation systems. Particularly, the present invention is directed to systems that fixate a portion of the skull, typically the occipital bone, to a portion of the spine for correction, fixation, and/or stabilization of a human spine.

2. Description of Related Art

Spinal fixation, such as lumbar sacral fusion and the correction of spinal deformities such as scoliotic curves, is a well known and frequently used medical procedure. Pedicle, lateral, and oblique mounting devices can be used to secure corrective spinal instrumentation to a portion of the spine that has been selected to be fused by arthrodesis.

A spinal fixation system typically includes corrective spinal instrumentation that is attached to selected vertebra of the spine by screws, hooks, and clamps. The corrective spinal instrumentation includes spinal rods or plates that are generally parallel to the patient's back. The corrective spinal instrumentation can also include transverse connecting rods that extend between neighboring spinal rods. Spinal fixation systems are used to correct problems in the lumbar and thoracic portions of the spine, and are often installed posterior to the spine on opposite sides of the spinous process and adjacent to the transverse process.

Various types of screws, hooks, and clamps have been used for attaching corrective spinal instrumentation to selected portions of a patient's spine. Examples of pedicle screws and other types of attachments are illustrated in U.S. Pat. Nos. 4,763,644; 4,805,602; 4,887,596; 4,950,269; and 5,129,388. Each of these patents is incorporated by reference as if fully set forth herein.

Fixation of the skull to the cervical spine can be used to treat trauma to the neck, degenerative diseases such as rheumatoid arthritis, and pain that is otherwise unresponsive to treatment. Current implantable devices designed to immobilize the skull with respect to the upper cervical spine have to be individually tailored. Often, such devices are assemblies of several components not designed specifically for fusing the cervical spine to the skull. However, devices specifically designed for fusing the cervical spine to the skull are currently being introduced. U.S. Pat. No. 6,146,382 issued to John Hurlbert on Nov. 14, 2000, shows one such device, the contents of this patent being incorporated herein by reference as if full set forth herein.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention includes a system for fixing a region of the skull to a portion of the spine. The system includes a plate configured to contact a region of the skull and be secured thereto. The plate has a top surface and at least one elongated slot defined therein. The at least one elongated slot has a transverse dimension. A threaded opening is provided in the plate in communication with the elongated slot. The system further includes an adjustable housing having a body portion and a base portion. The body portion has a channel defined therein to receive a spinal rod. The base portion has a first cross dimension. The adjustable housing further includes a threaded exterior surface, and is configured to be received by the elongated slot. The threaded exterior surface of the adjustable housing is configured to be received in the threaded opening of the plate. The plate can include a recessed surface along at least a portion of the elongated slot opposite the top surface. The plate can further include a first interlocking surface disposed within the recessed surface, and the adjustable housing includes a second interlocking surface. The adjustable housing is configured to be positioned in a first position within the elongated slot such that the first and second interlocking surfaces are spaced apart so as to permit translational or rotational movement of the adjustable housing in the slot. The adjustable housing also has a second position in the elongated slot such that the second interlocking surface engages the first interlocking surface to secure at least one of translational and rotational movement of the adjustable housing. A bottom wall can be provided on the plate to enclose at least a portion of the recessed surface and define a cavity within which a base portion of the adjustable housing is captured when the adjustable housing is received in the elongated slot. The plate can further include at least one aperture to receive a fastener therethrough to secure the plate to a skull. The system also can include device to secure the rod within the adjustable housing. For example, a threaded securing device can be provided wherein the body portion of the adjustable housing includes a threaded surface to receive the securing device and secure a spinal rod within the channel.

In accordance with other aspects of the present invention, the invention includes a method for fixing a region of the skull to a portion of the spine. The method includes a securing a plate to a region of the skull. The plate has a top surface and at least one elongated slot defined therein. The at least one elongated slot has a transverse dimension. A threaded opening is provided in the plate in communication with the elongated slot. The method further includes an adjustable housing having a body portion and a base portion. The body portion has a channel defined therein to receive a spinal rod. The base portion has a first cross dimension. The adjustable housing further includes a threaded exterior surface, and is configured to be received by the elongated slot. The threaded exterior surface of the adjustable housing is configured to be received in the threaded opening of the plate. The plate can include a recessed surface along at least a portion of the elongated slot opposite the top surface. The plate can further include a first interlocking surface disposed within the recessed surface, and the adjustable housing includes a second interlocking surface. The adjustable housing is configured to be positioned in a first position within the elongated slot such that the first and second interlocking surfaces are spaced apart so as to permit translational or rotational movement of the adjustable housing in the slot. The adjustable housing also has a second position in the elongated slot such that the second interlocking surface engages the first interlocking surface to secure at least one of translational and rotational movement of the adjustable housing. A bottom wall can be provided on the plate to enclose at least a portion of the recessed surface and define a cavity within which a base portion of the adjustable housing is captured when the adjustable housing is received in the elongated slot. The plate can further include at least one aperture to receive a fastener therethrough to secure the plate to a skull. The method also can include device to secure the rod within the adjustable housing. For example a threaded securing device can be provided wherein the body portion of the adjustable housing includes a threaded surface to receive the securing device and secure a spinal rod within the channel.

The first interlocking surface and the second interlocking surface can be formed of a variety of configurations, such as a series of extending projections configured for mating engagement. Alternatively, the first interlocking surface and the second interlocking surface can be configured to form a cold weld when the adjustable housing is fixed in position. The plate also can include a lip extending from the top surface along at least a portion of the elongated slot.

It is to be understood that both the foregoing general description and the following detailed description are exemplary and are intended to provide further explanation of the invention claimed.

The accompanying drawings, which are incorporated constitute part of this specification, are included to illustrate and provide a further understanding of the method and system of the invention. Together with the description, the drawings serve to explain the principles of the invention.

DETAILED DESCRIPTION OF THE PREFERRED EMBODIMENT

Reference will now be made in detail to the present preferred embodiments of the invention, an example of which is illustrated in the accompanying drawing. The method and corresponding steps of the invention will be described in conjunction with the detailed description of the system.

In accordance with one aspect of the invention, a system is provided for fixing a region of the skull to a portion of the spine. The system includes a plate configured to contact a region of the skull and be secured thereto. The plate has a top surface and at least one elongated slot defined therein. The elongated slot has a transverse dimension and a perimeter edge, and the plate preferably has a first interlocking surface disposed proximate the perimeter edge.

Figure 1:
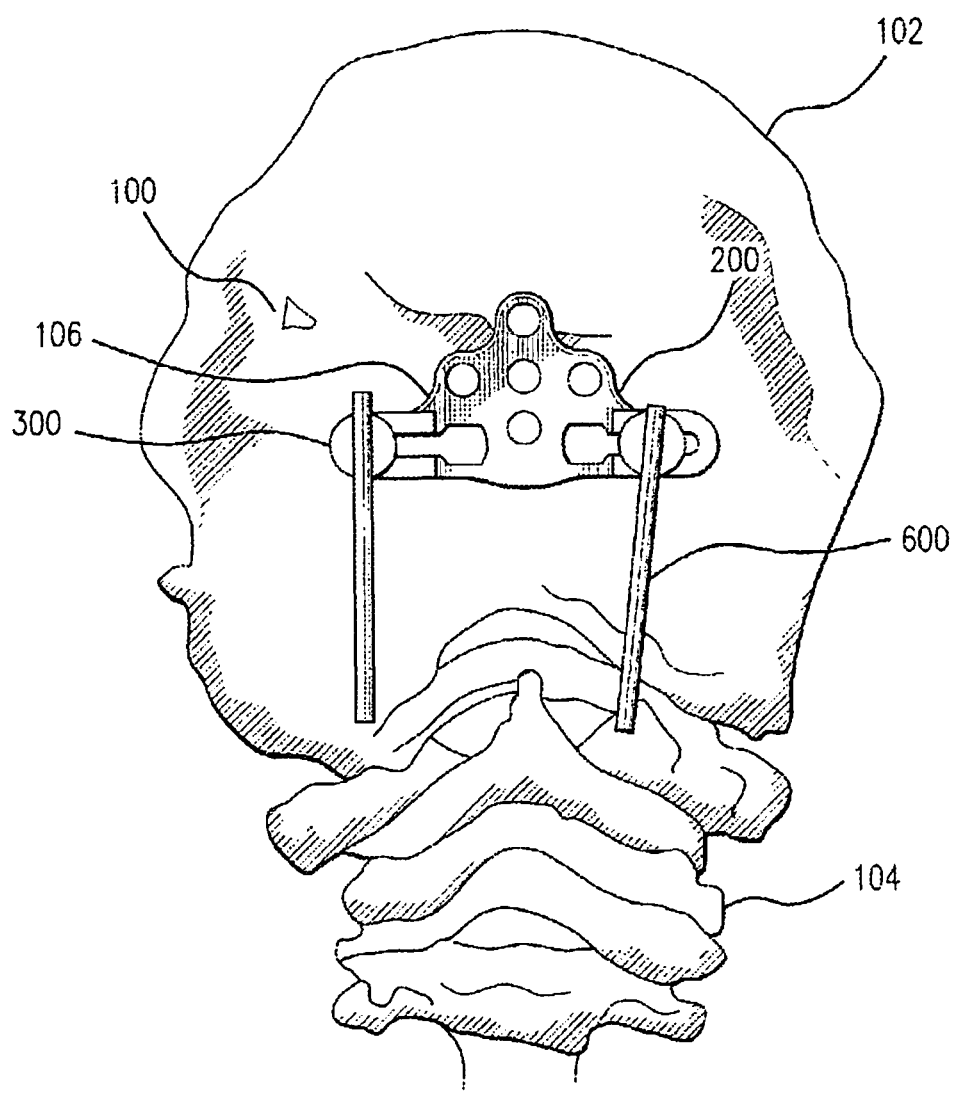
FIGS. 1 and 2 depict an occipito-cervical spinal fixation system embodying the present invention in use with FIG. 1 being a view looking upward along a portion of a spinal column toward an occiput of a skull, and FIG. 2 being a lateral view.
Figure 2:
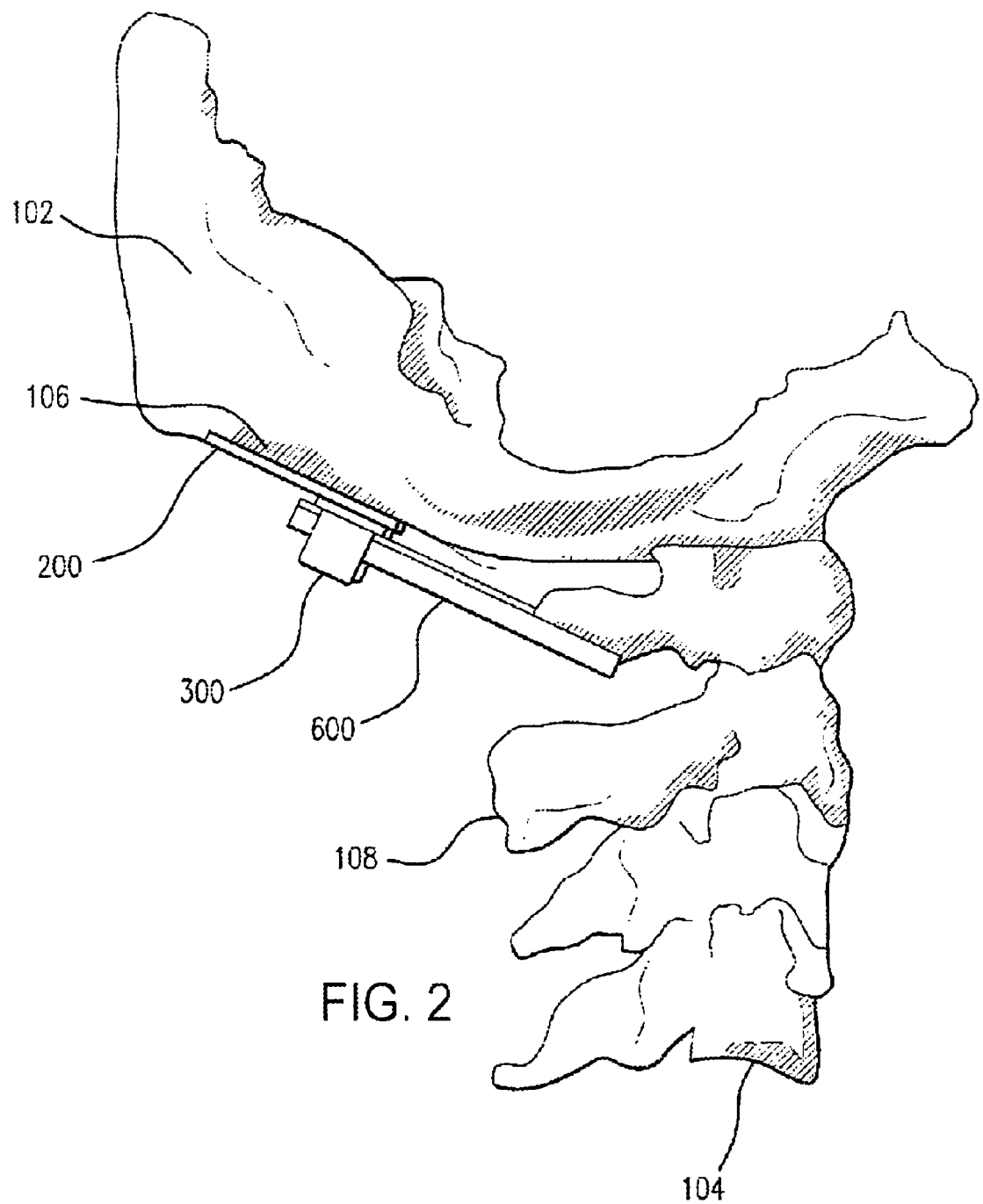

For purpose of context and illustration, but not limitation, FIGS. 1 and 2 show an occipito-cervical spinal fixation system 100 of the invention for mechanically fixing a region of a skull 102 to a portion of a spinal column 104. The system 100 includes a plate 200 as described further below. Also depicted in FIGS. 1 and 2 for the purpose of context and illustration in accordance with additional aspects of the invention are at least one spinal rod 600, (but more typically two of the spinal rods 600) and an adjustable housing 300, for each spinal rod 600.

The plate 200 is configured to contact the occiput or occipital bone 106 of the skull 102 and be secured thereto. The spinal rod 600 is configured to extend from a location adjacent the plate 200 for connection thereto to a location adjacent at least one of the vertebra 108 of the spine 104 for connection thereto (not shown). An adjustable housing 300 is configured to connect the rod 600 to the plate 200, as described further below. In this regard the components of the fixation system are preferably configured to substantially immobilize the skull 102 with respect to the spinal column 104. The components of the fixation system 100 are preferably made from a suitable biocompatible material, such as titanium or stainless steel.

As shown in FIGS. 3-5d, 15, and 17-20, the plate 200 preferably includes one or more of openings 202 formed therein for receiving connecting members 204 (not shown). During use, connecting members 204 can be inserted into holes formed in the skull 102 to secure the plate 200 to the occiput 106 such that movement of the skull 102 with respect to a portion of the spine is inhibited. In this regard, connecting members 204 preferably are a suitable bone screw or anchor, many configurations of which are known.

While any suitable shape can be used for the plate 200, it is preferred that the plate 200 have a shape that generally conforms to the occiput 106, with the illustrated generally triangular configuration being highly preferred because it offers multiple options for placement of the openings 202 and the associated connecting members 204. The generally triangular configuration can include an inverted T, an inverted V, or a horseshoe shape among others. It is preferred that the plate 200 include a central portion that extends longitudinally to provide one or more possible locations for the openings 202 and the associated connecting members 204 central to the occiput 106. One or more arms can be defined by the plate to accommodate elongated slots as described below.

Figure 3:
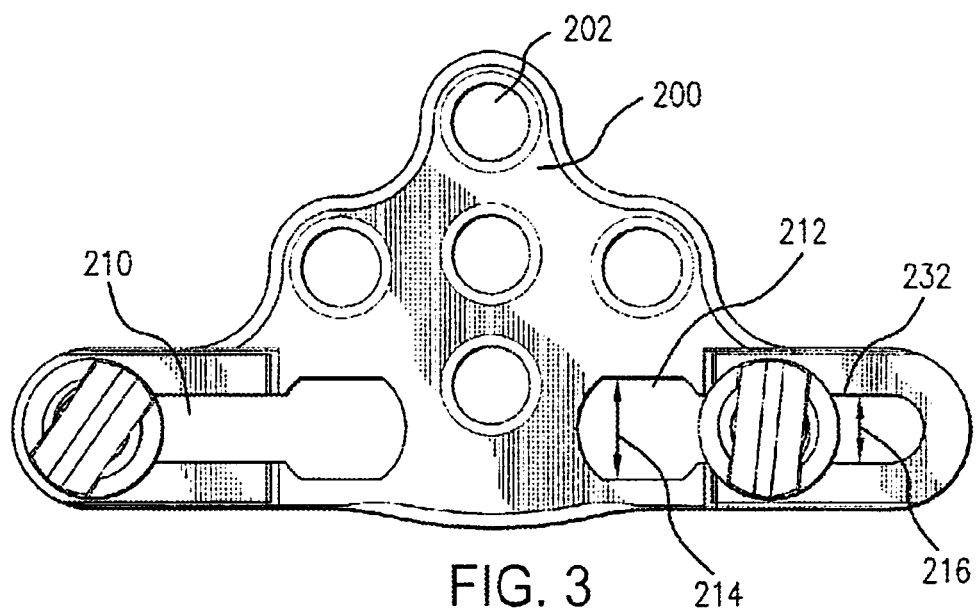
FIG. 3 is a top view of selected components of the fixation system.
Figure 5A:
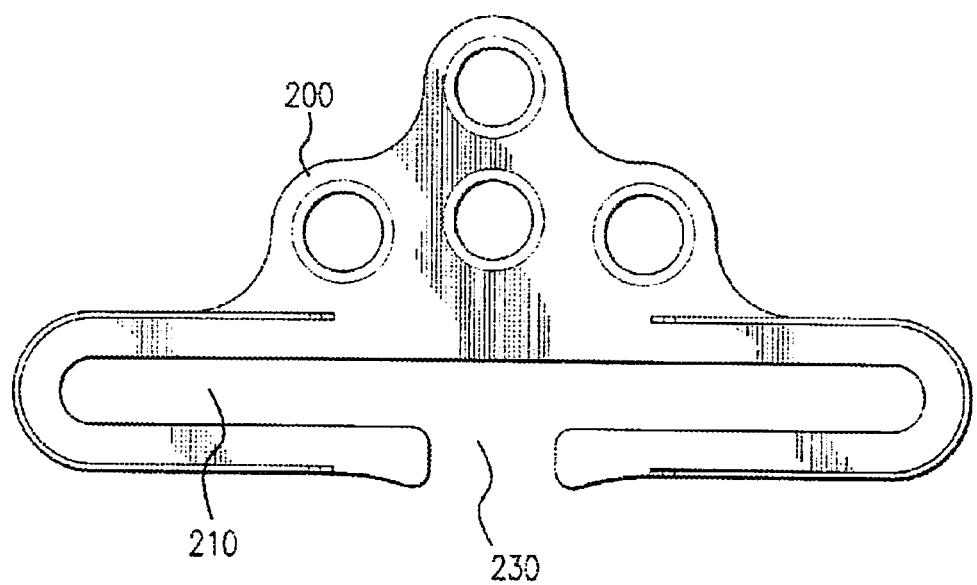
FIG. 5a is a top view of an alternate embodiment of the plate of the fixation system.
Figure 5B:
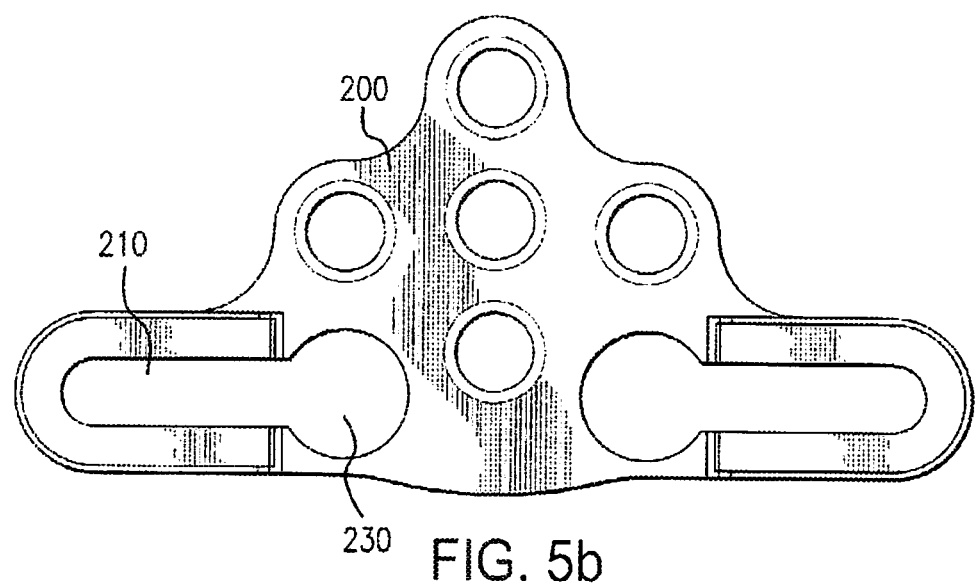
FIG. 5b is a top view of an alternate embodiment of the plate of the fixation system.
Figure 5C:
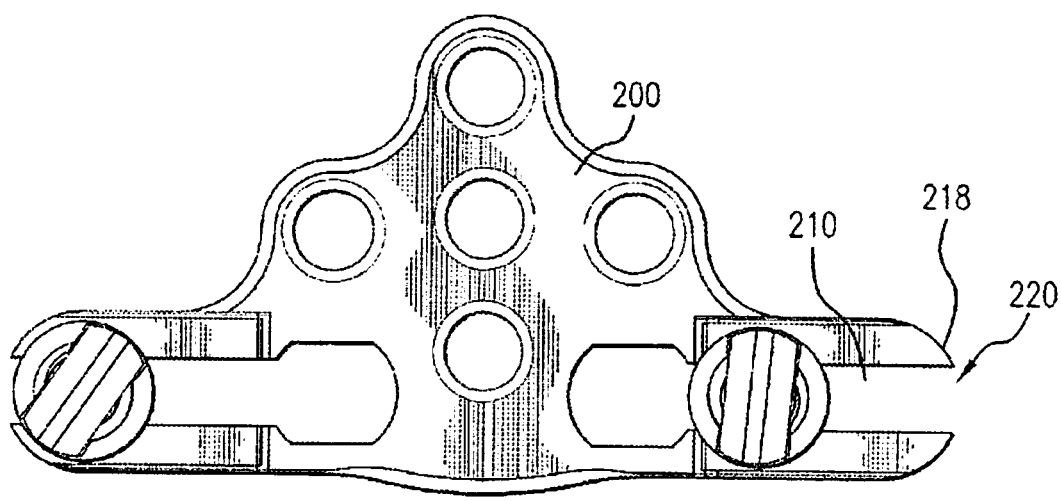
FIG. 5c is a top view of an alternate embodiment of selected components of the fixation system.
Figure 5D:
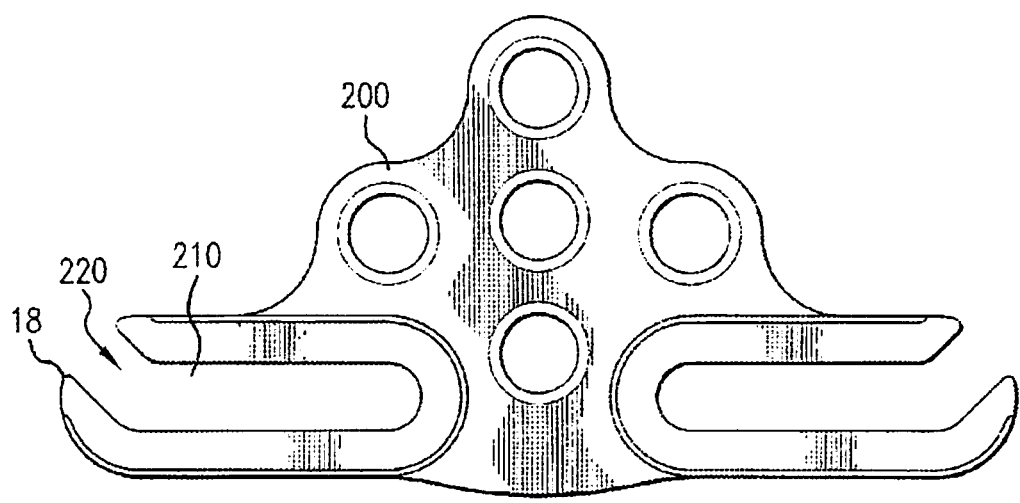
FIG. 5d is a top view of another alternate embodiment of the plate of the fixation system.
Figure 6:
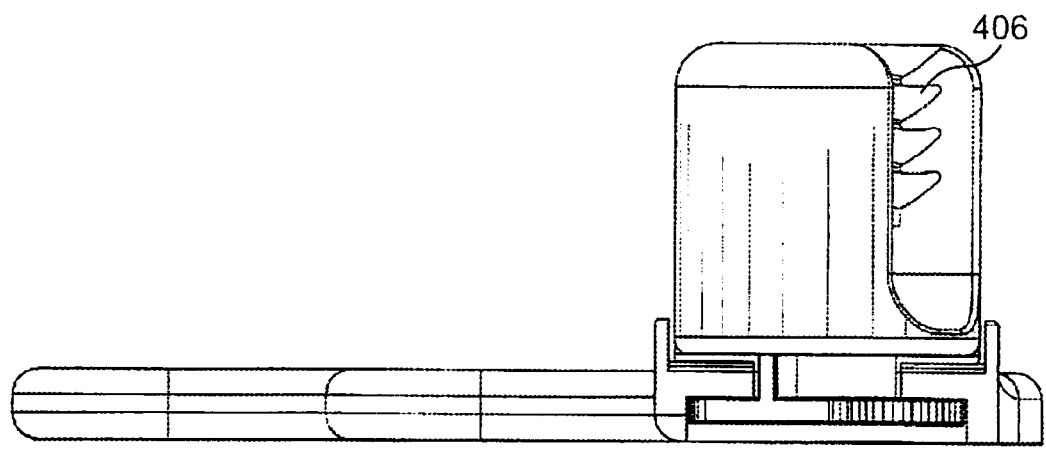
FIG. 6 is a partial cross-sectional side view of an embodiment of selected components of the fixation system.
Figure 7:
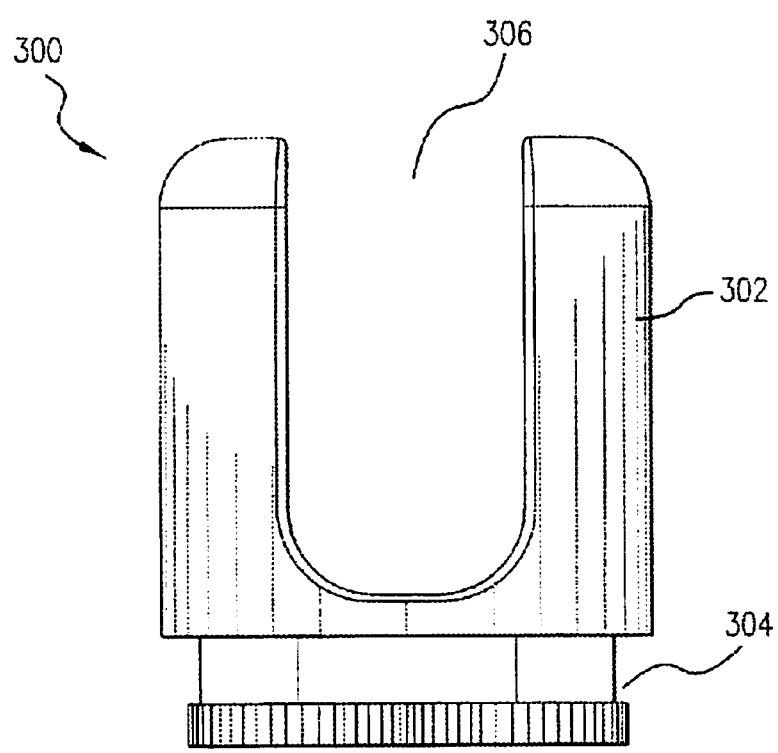
FIG. 7 is a front view of an adjustable housing of the fixation system.
Figure 8:
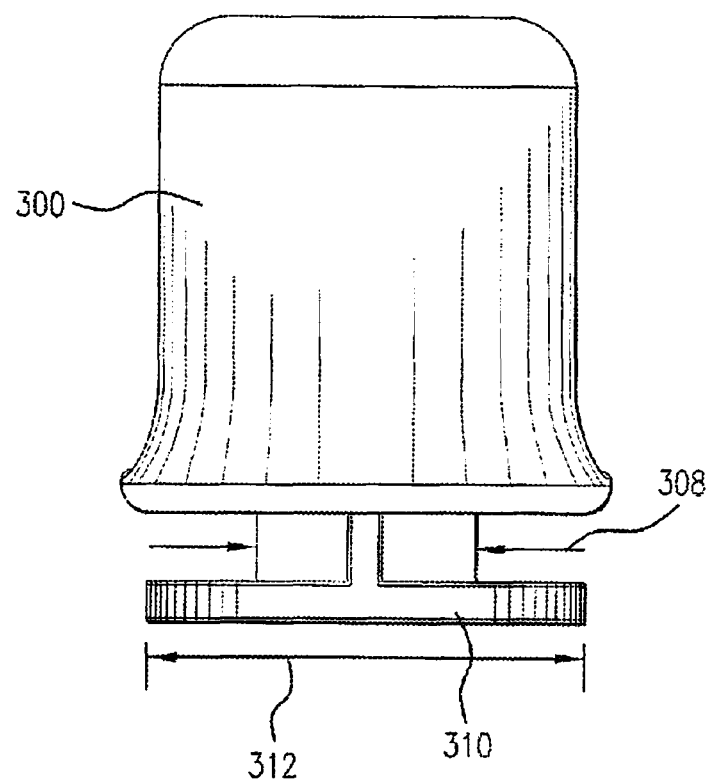
FIG. 8 is a side view of an adjustable housing of the fixation system.
Figure 9:
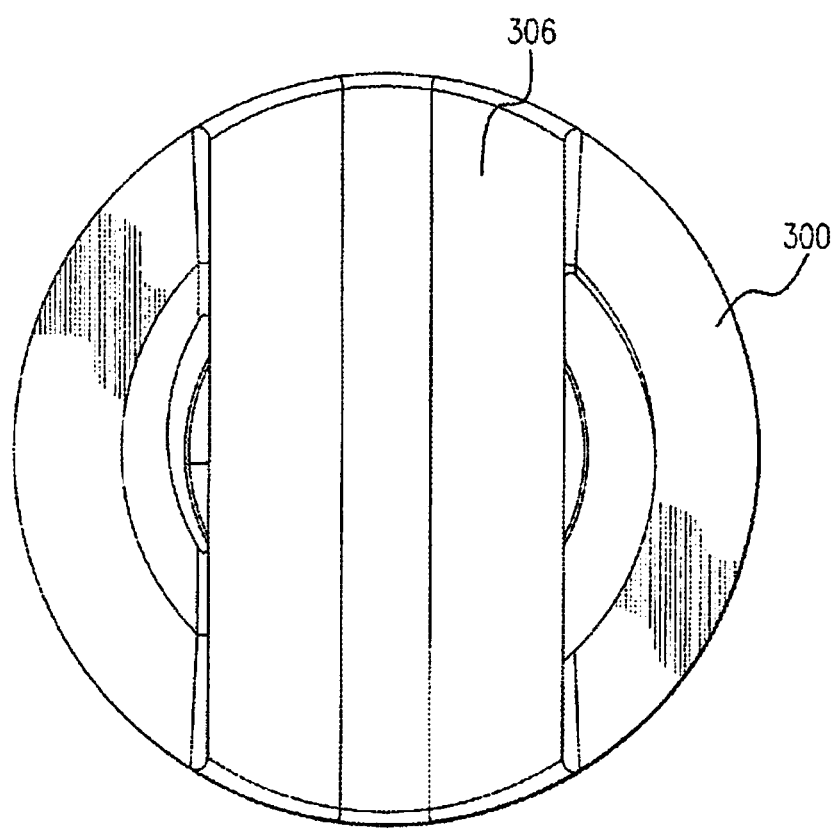
FIG. 9 is a top view of an adjustable housing of the fixation system.
Figure 17:
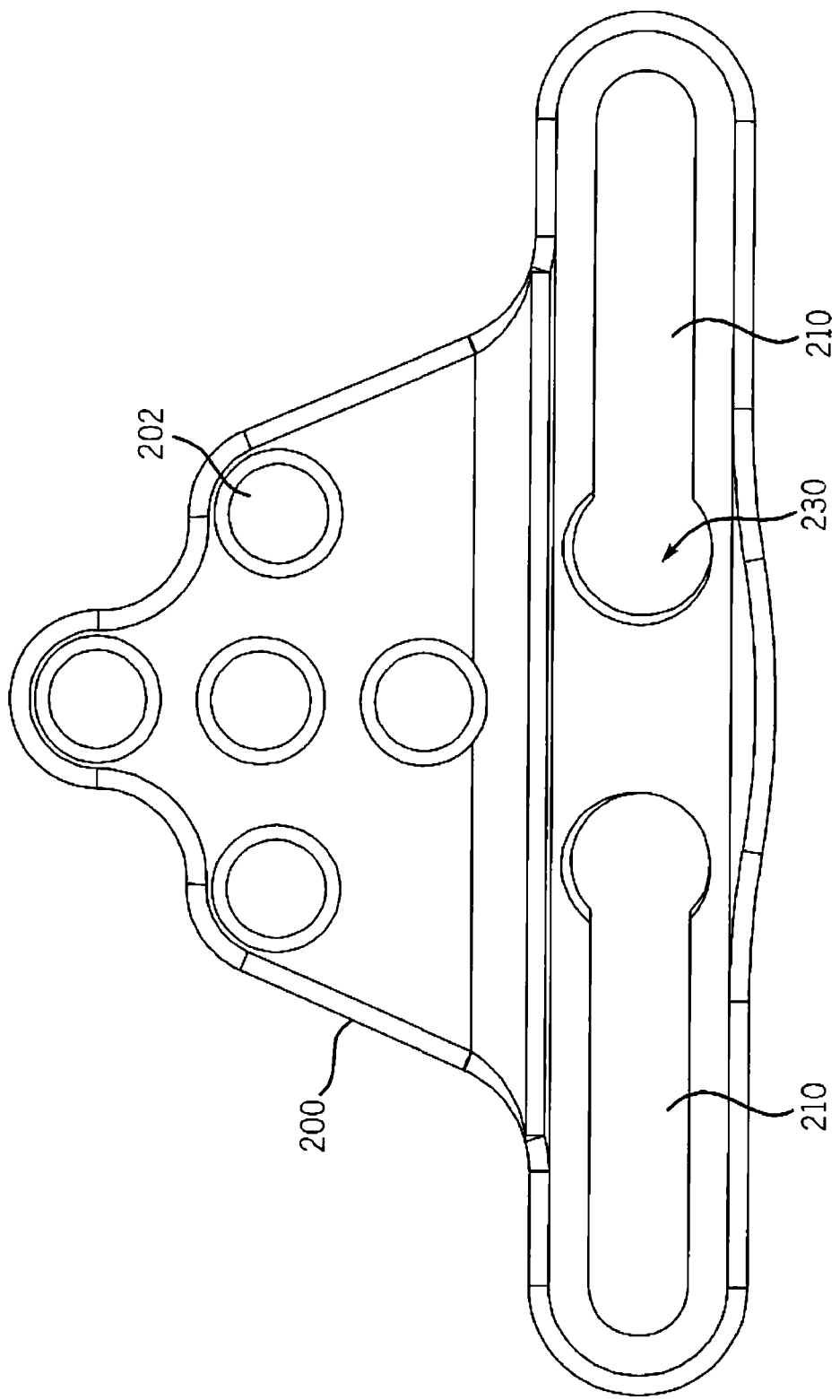
FIG. 17 is a top view of an alternate embodiment of the plate of the fixation system.

The plate 200 has at least one elongated slot 210, and preferably has two elongated slots 210 as shown, for example, in FIGS. 3 and 17. Each elongated slot 210 has a transverse dimension 216 and a perimeter edge. Preferably, an opening is provided in communication with the elongated slot for receipt of an adjustable housing therein. For example, the plate 200 can include a keyed opening 212 at the perimeter edge of the elongated slot as shown in FIG. 3 for receipt of an adjustable housing in a specific orientation. Alternatively the elongated slot 210 can extend to an edge of the plate 200 to define an opening 220 therein for receipt of an adjustable housing from a side of the plate as shown in FIGS. 5c, 5d, and 6. In another embodiment of the invention, the plate 200 can include an aperture 230 in communication with the elongated slot 210. FIG. 5b illustrates a configuration in which an enlarged aperture 230 is in communication with each elongated slot 210 for positioning an adjustable housing in the slot from a top surface of the plate. FIG. 5a illustrates a configuration in which a central aperture 230 is in communication with two elongated slots 210 and, if desired, extends to the outside edge of the plate 200. In this manner, an adjustable housing 300 can be positioned in the aperture from either a top or side surface of the plate, and then moved into the elongated slot 210.

Figure 4:
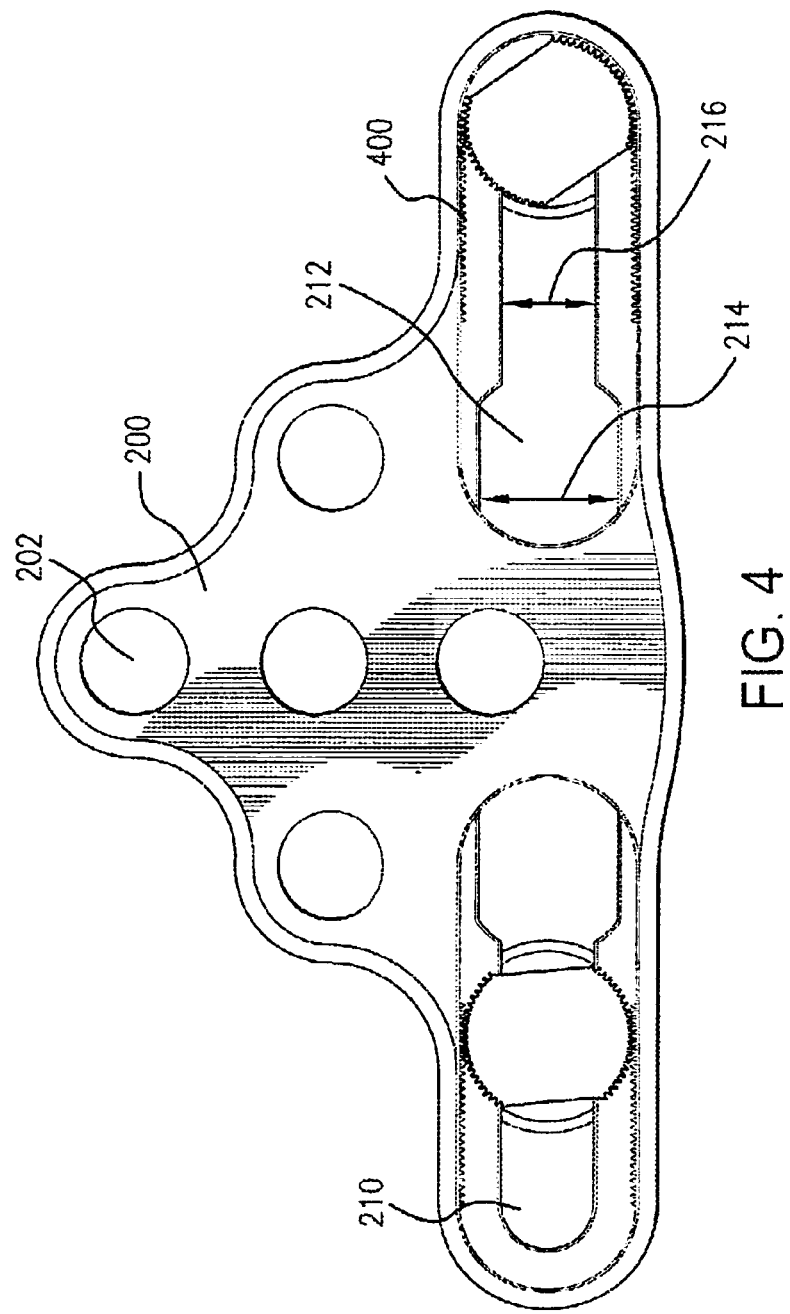
FIG. 4 is a bottom view of the selected components of the fixation system of FIG. 3.

In accordance with one aspect of the invention, the plate 200 includes first interlocking surface 400. The first interlocking surface 400 can be disposed in a recess formed in the plate opposite the top surface, as shown in FIG. 4. Alternatively, first interlocking surface 400 can be disposed proximate or along the perimeter edge of the elongated slot 210. The first interlocking surface 400 can be disposed proximate the perimeter edge underneath the surface of the plate 200 or in an enclosed slot as will be further disclosed below.

Further in accordance with the invention, and as noted the system for fixing a region of the skull to a portion of the spine includes an adjustable housing having a body portion and a base portion. The base portion of the adjustable housing has a first cross dimension and a flange with a second cross dimension extending outwardly from the base portion. A second interlocking surface is provided on the adjustable housing to engage the first interlocking surface of the plate. The adjustable housing is configured to be received by the elongated slot. The first cross dimension of the base portion is less than the transverse dimension of the elongated slot and the second cross dimension of the flange is greater than the transverse dimension of the elongated slot.

In order to facilitate placement of the adjustable housing 300 within the elongated slot 210 of the plate 200, as previously noted, an opening is provided in communication with the slot. In one embodiment of the invention, as shown in FIGS. 3 and 4, the plate 200 includes a keyed opening 212 in communication with the elongated slot 210. The keyed opening 212 having a transverse dimension 214 greater than transverse dimension 216 of the elongated slot to facilitate receipt of the adjustable housing 300 therein. In this manner, the adjustable housing can be inserted into the keyed opening from the top and then moved laterally into the elongated slot. If desired, the keyed opening can be configured to require the adjustable housing to be rotated prior to such lateral movement. The plate can further include a lip between the keyed opening and the elongated slot to inhibit inadvertent release of the adjustable housing 300 from the elongated slot 210.

Alternatively, the plate 200 can be provided with an aperture 230, which defines an opening in elongated slot 210 as shown in FIGS. 5a and 5b. In the configuration illustrated in FIG. 5a, the aperture is in communication with an edge of the plate, such that the adjustable housing 300 can be inserted laterally from the edge of the plate into the slot, or from the top surface as desired. In the configuration illustrated in FIG. 5b, adjustable housing 300 can be inserted from the top and then moved laterally into elongated slot 210.

In another embodiment of the invention, as shown in FIGS. 5c and 5d, the elongated slot 210 extends directly to an edge 218 of the plate for forming an opening 220 for receipt of the adjustable housing 300. The top surface of the plate can include a lip proximate the opening to inhibit inadvertent release of the adjustable housing 300 from the elongated slot 210.

The plate 200 can further include a raised lip 232 extending from the top surface along at least a portion of the elongated slot to form a guide for translational movement of the adjustable housing, as shown in FIG. 3.

As shown in FIGS. 5a-d and 6, the plate 200 can further include a recessed surface along at least a portion of the elongated slot 210 opposite the top surface. In a preferred embodiment, the first interlocking surface can be disposed within the recessed surface. The elongated slot 210 can extend through the depth of the plate 200 as shown in FIG. 5d, or the plate 200 can further include a bottom wall 222, shown in FIG. 15, to enclose at least a portion of the recessed surface and define a cavity within which the flange of the adjustable housing 300 is captured when the adjustable housing 300 is received within the elongated slot 210.

For purpose of illustration, but not limitation, the adjustable housing 300, shown in detail in FIGS. 7-10 and 16 includes a body portion 302 and a base portion 304. The body portion 302 includes an internal cavity 306 for receipt of a spinal rod. The internal cavity 306 can have threads 406 (as shown in FIGS. 6, 11a, 14a, and 14b) therein for receiving a securing device 500 (shown in FIGS. 21 and 22). In accordance with one aspect of the invention, the base portion 304 has a first cross dimension 308 that is smaller than the transverse dimension 216 of the elongated slot 210 of the plate. The base portion 304 of the adjustable housing 300 includes a flange 310 extending therefrom. The flange 310 has a second cross dimension 312 greater than the transverse dimension 216 of the elongated slot 210. As embodied herein the flange further includes a second interlocking surface 402 as shown for example in FIGS. 11-14b. The adjustable housing 300 is configured for receipt in the elongated slot 210 of plate 200 as shown for example in FIG. 11.

Figure 10:
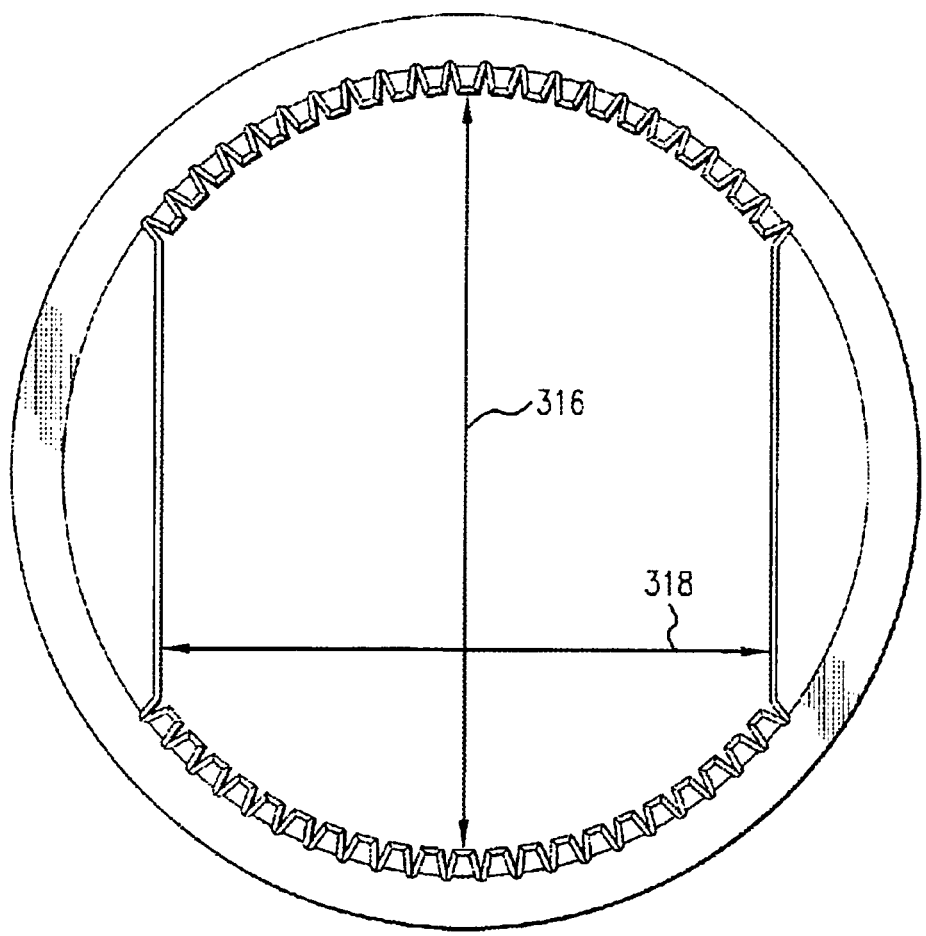
FIG. 10 is a bottom view of an adjustable housing of the fixation system.
Figure 11A:
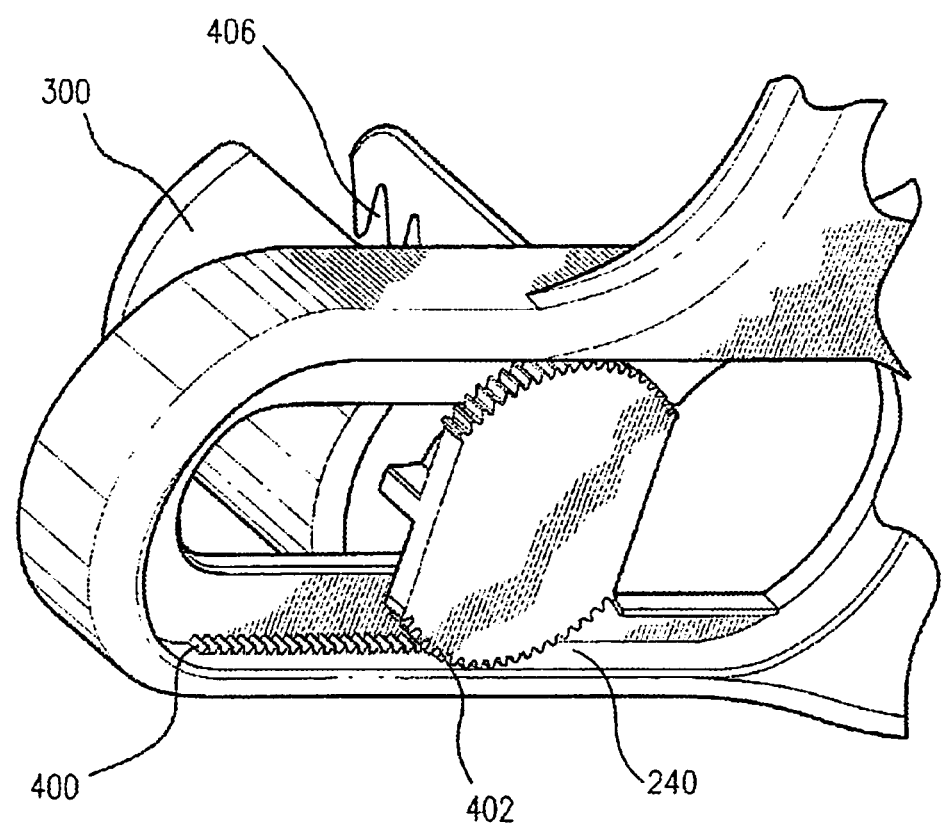
FIG. 11a is an enlarged perspective view showing selected components of the fixation system with the adjustable housing in a first position.
Figure 11B:
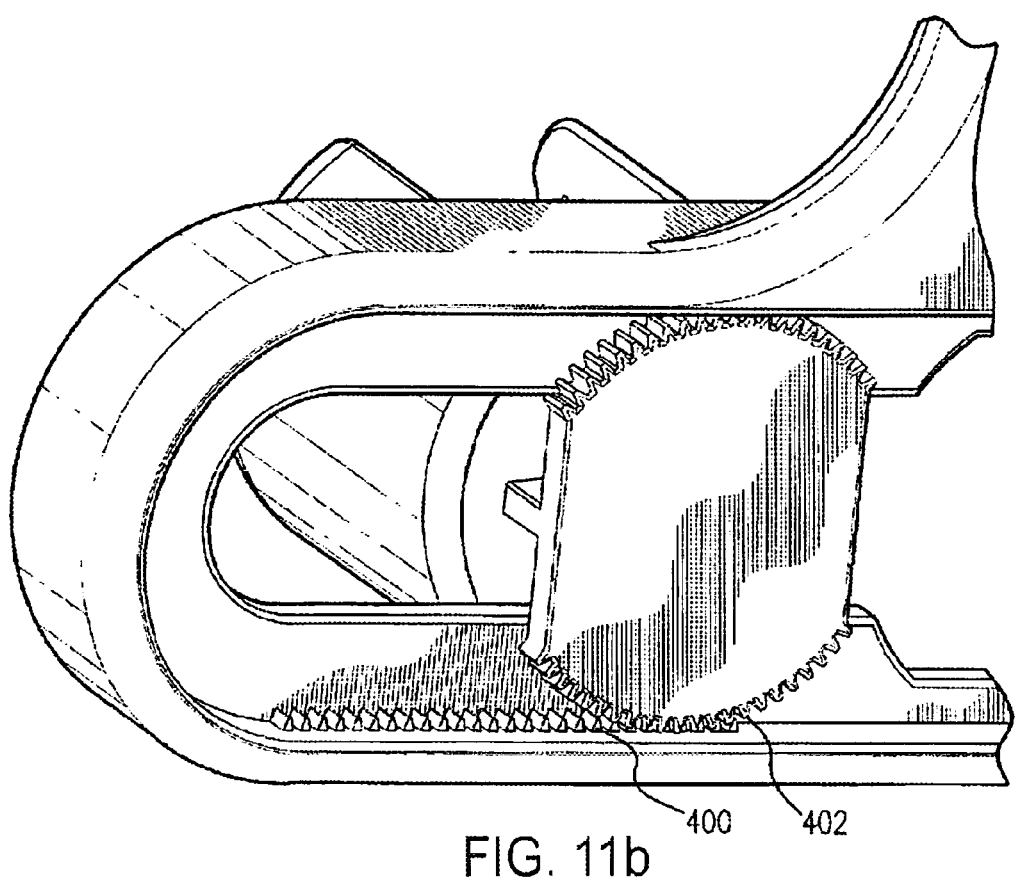
FIG. 11b is an enlarged perspective view showing selected components of the fixation system with the adjustable housing in a second position.

In an embodiment of the invention, as shown in FIGS. 10, 11a, and 11b, the flange 310 has two different cross dimensions. The greater of the two cross dimension 316 being the full diameter of the flange 310 at its edge; the smaller of the two cross dimensions 318 being the width of the flange 310 between its straight side edges, as depicted. This flange profile allows for the adjustable housing 300 to be placed in a predetermined orientation into the keyed opening 212 such that the straight edges of the flange are parallel with the edges of the elongated slot 210. The adjustable housing 300 can thus be slid into the elongated slot 210 and rotated so that the straight edges of the flange 310 are angled relative to the edges of the elongated slot 210. In this rotated position, the flange 310 will be inhibited from being released from the slot.

Figure 12:
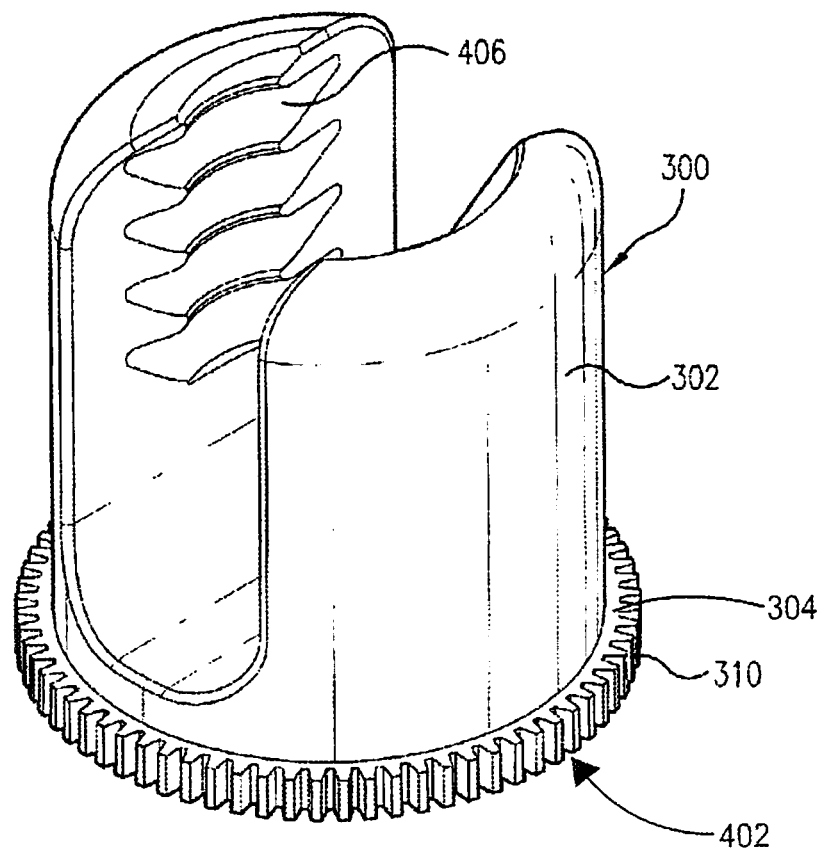
FIG. 12 is a perspective view of an alternate embodiment of an adjustable housing of the fixation system.

In another embodiment of the invention, as shown in FIG. 12, the base portion 304 can have a circular cross section and if desired, the same or similar dimensions as the body part. Furthermore, the adjustable housing 300 can have a flange 310 that can be any of a variety of shapes depending upon the configuration of the opening to the slot. For example, as shown, the flange 310 can be circular if an aperture is provided of sufficient size for access to the slot, or if the slot extends to an edge of the plate.

The adjustable housing 300 can be of a single piece construction or can be an assembly of multiple pieces as desired and needed, and made of suitable material.

In accordance with another aspect of the present invention, as shown in FIG. 11a, the adjustable housing 300 has a first position within the elongated slot 210 in which the second interlocking surface 402 is spaced apart from the first interlocking surface 400 to permit at least one of translational and rotational movement of the adjustable housing 300 relative to the plate 200. As shown in FIG. 11b, the adjustable housing 300 further has a second position within the elongated slot 210 in which the second interlocking surface 402 is in engagement with the first interlocking surface 400 in order to secure at least one of translational and rotational movement of the adjustable housing 300.

For example, for purpose of illustration and not limitation, as shown in FIG. 11a the adjustable housing 300 can be disposed within the elongated slot in a first position in which the first and second interlocking surfaces 400 and 402, respectively are spaced apart from each other in order to permit translational and rotational movement of the adjustable housing 300 relative to the plate 200.

Figure 13:
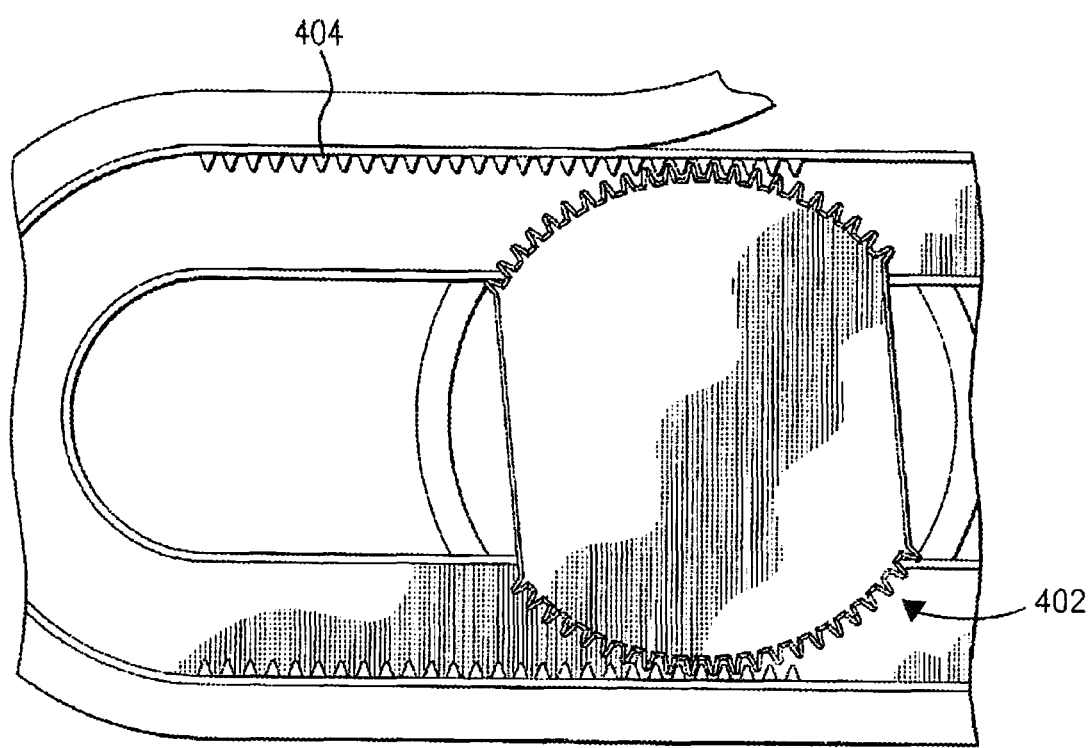
FIG. 13 is an enlarged partial bottom view showing selected components of the fixation system of FIG. 11b.

Once the adjustable housing 300 is properly located for placement of the spinal rod 600, the adjustable housing 300 can be moved to a second position as shown in FIGS. 11b and 13, in which the first and second interlocking surfaces 400 and 402, respectively, are in engagement to secure at least one of, and preferably both, translational and rotational movement of the adjustable housing 300.

Figure 16:
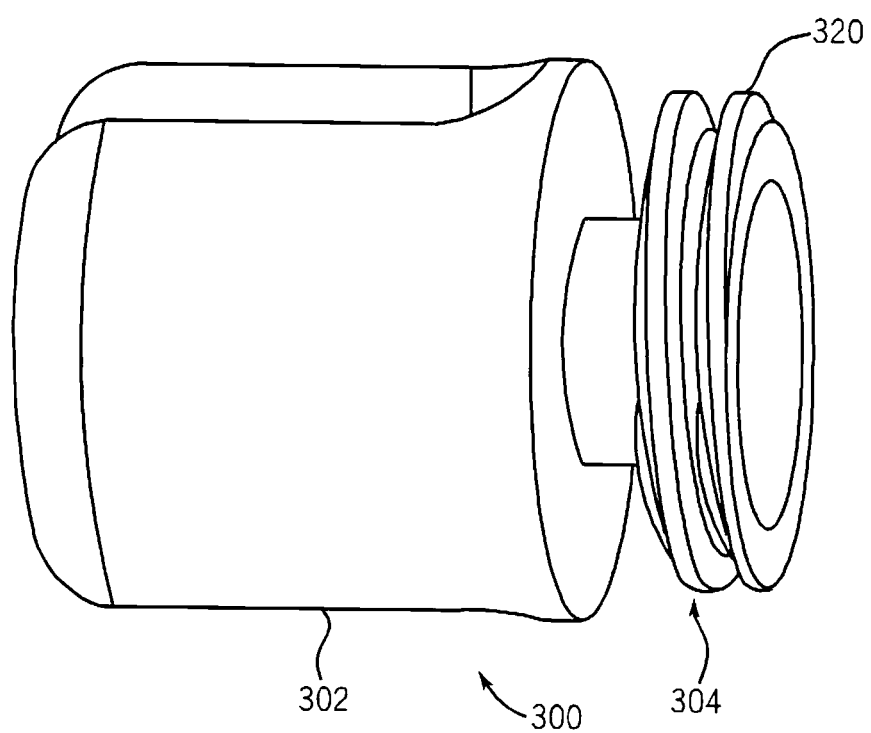
FIG. 16 is a perspective view of an alternate embodiment of an adjustable housing having a threaded base.

In accordance with another aspect of the invention, as shown in FIG. 16, the adjustable housing 300 can include a base 304 having exterior threads 320 thereon. The exterior threads 320 are configured to mate with threaded aperture 230 of plate 200 as shown in FIGS. 17-20. The threads can be of any suitable type known in the art. For example, the threads of exterior threads 320 and corresponding threaded aperture 230 can be V-shaped threads, helical threads, saw toothed threads, buttress threads, or flat-end threads. The threads can be at any suitable angle and depth as desired.

Figure 18:
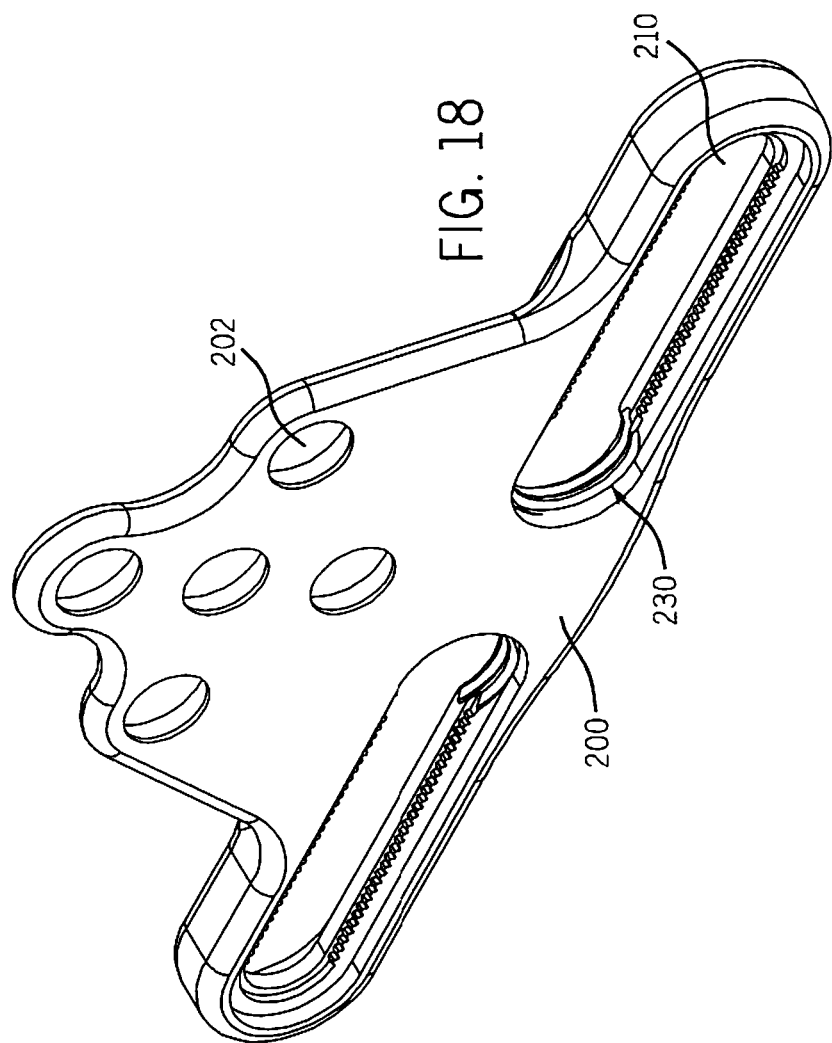
FIG. 18 is a perspective view of an alternate embodiment of the plate of the fixation system.
Figure 19:
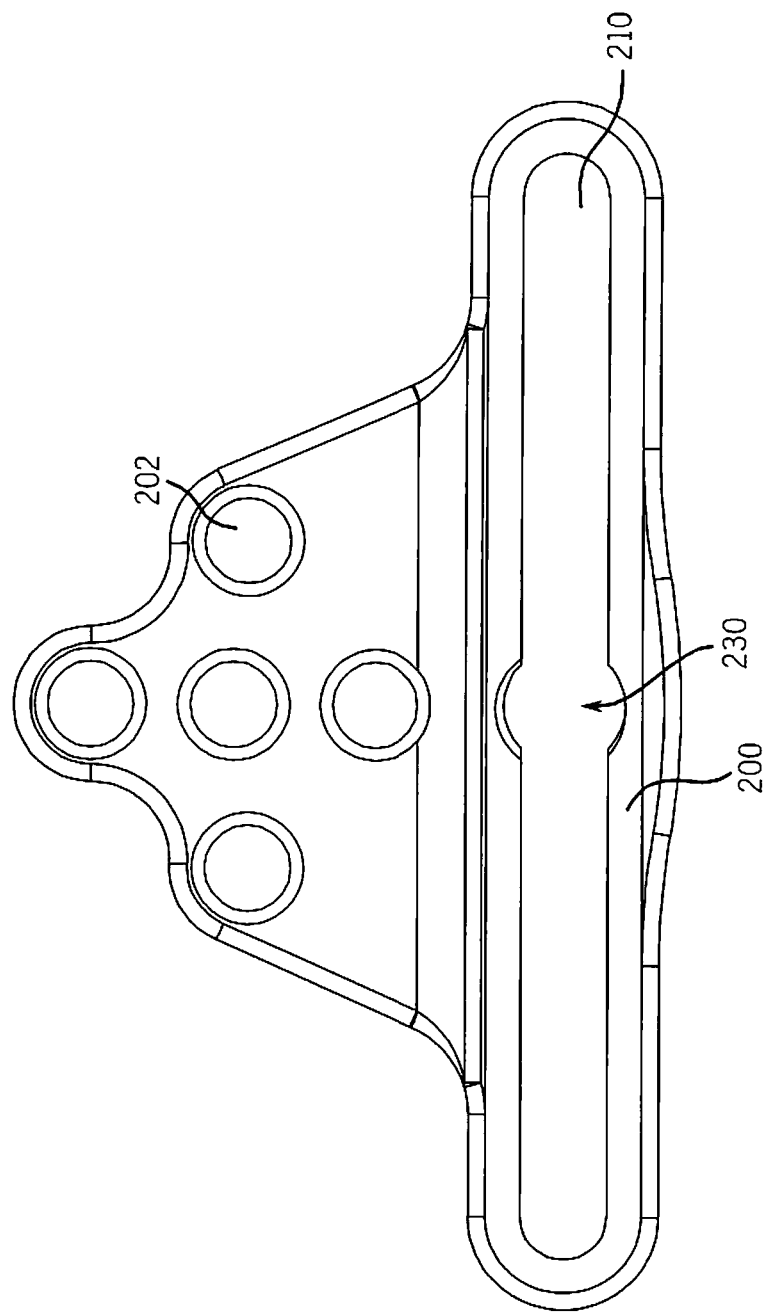
FIG. 19 is a top view of another embodiment of the plate of the fixation system.
Figure 20:
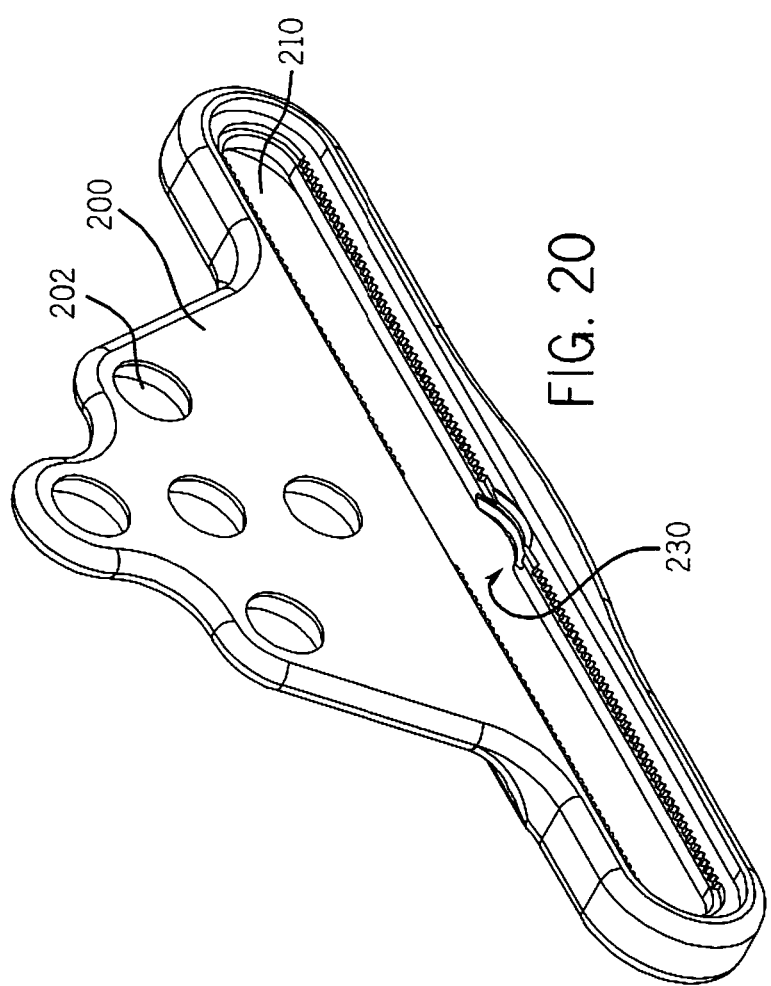
FIG. 20 is a perspective view of another embodiment of the plate of the fixation system.

In accordance with one aspect of the invention as shown in FIGS. 17-20, the plate 200 has at least one elongated slot 210. Preferably a threaded aperture 230 is provided in communication with the elongated slot 210 for receipt of an adjustable housing 300 therein. For example, as shown in FIGS. 19 and 20, the plate 200 can have a single elongated slot 210 with a threaded aperture 230 intermediate the ends of the elongated slot 210. Alternatively, as shown in FIGS. 17 and 18, the plate 200 can have two elongated slots 210, each having a threaded aperture 230 for receipt of an adjustable housing. The threaded aperture 230 can be disposed at any desired location along the length of the slot 210 although it is preferred to locate the threaded aperture 230 at one end of the slot 210. In this manner, an adjustable housing 300 can be threaded fully through the threaded aperture 230 until the flange is disposed below the threaded aperture. Once the adjustable housing 300 has been fully threaded through the threaded aperture 230, adjustable housing 300 can be slid or otherwise moved laterally into the elongated slot 210 until positioned as desired. Additionally, the adjustable housing 300, once received in the elongated slot 210 can not be removed from the slot without aligning it with the threaded aperture 230 and unthreading the adjustable housing 300. Therefore, the adjustable housing 300 once received in the elongated slot 210 may be moved along the length of the slot 210 without risk of becoming inadvertently dislodged.

In accordance with an additional aspect of the invention, as shown for example in FIG. 11a, the plate 200 of each embodiment can include a recessed surface 240 along at least a portion of the elongated slot 210 opposite the top surface of the plate 200. The plate 200 can further include a first interlocking surface 400 disposed within the recessed surface 240. Alternatively, the first interlocking surface 400 can be disposed proximate the perimeter edge underneath the surface of the plate 200 or in an enclosed slot. In accordance with one aspect of the invention, the adjustable housing 300 can include a flange having a second interlocking surface 402 thereon to engage the first interlocking surface 400 of the plate 200.

Figure 14A:
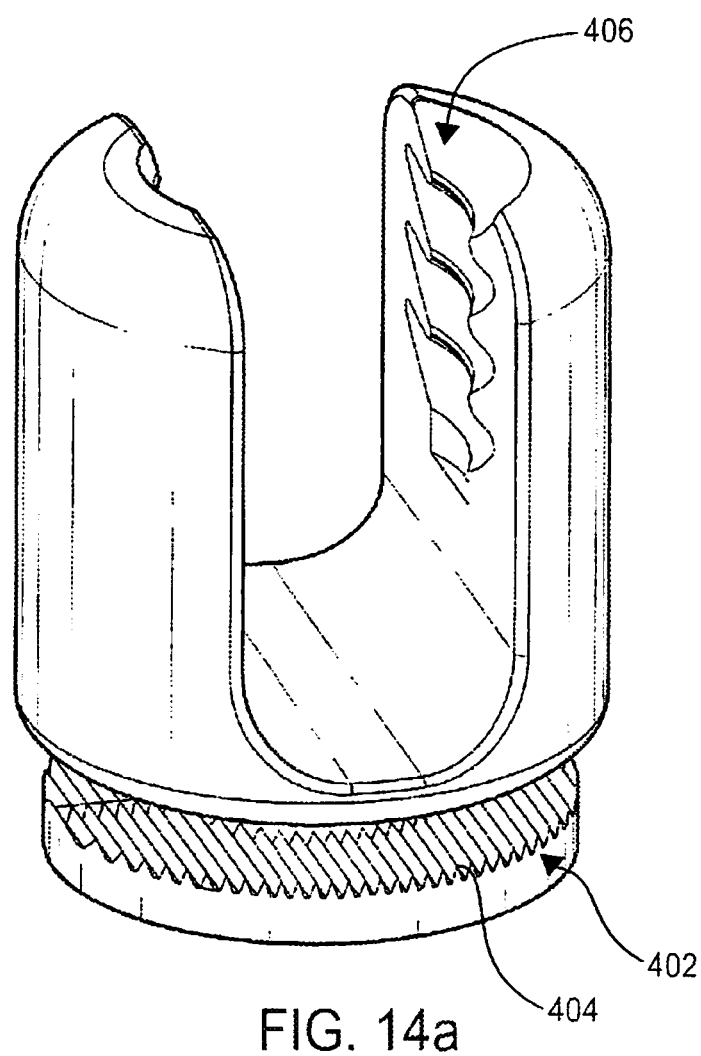
FIG. 14a is a perspective view of another embodiment of an adjustable housing of the fixation system.
Figure 14B:
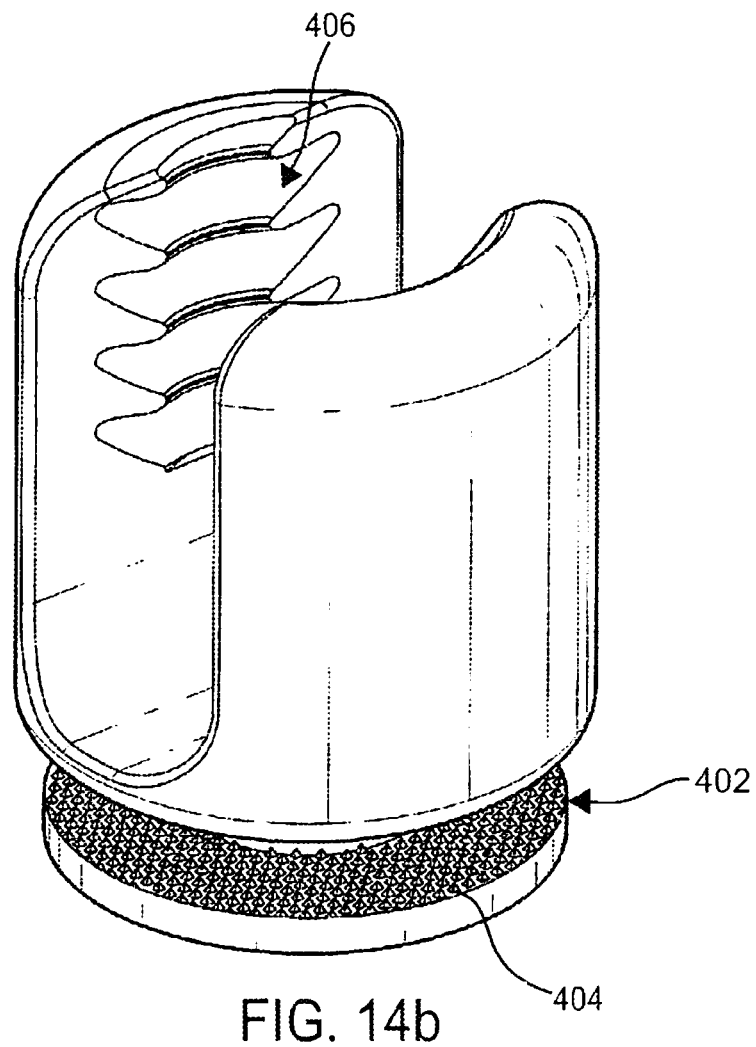
FIG. 14b is a perspective view of an alternative embodiment of an adjustable housing of the fixation system.
Figure 15:
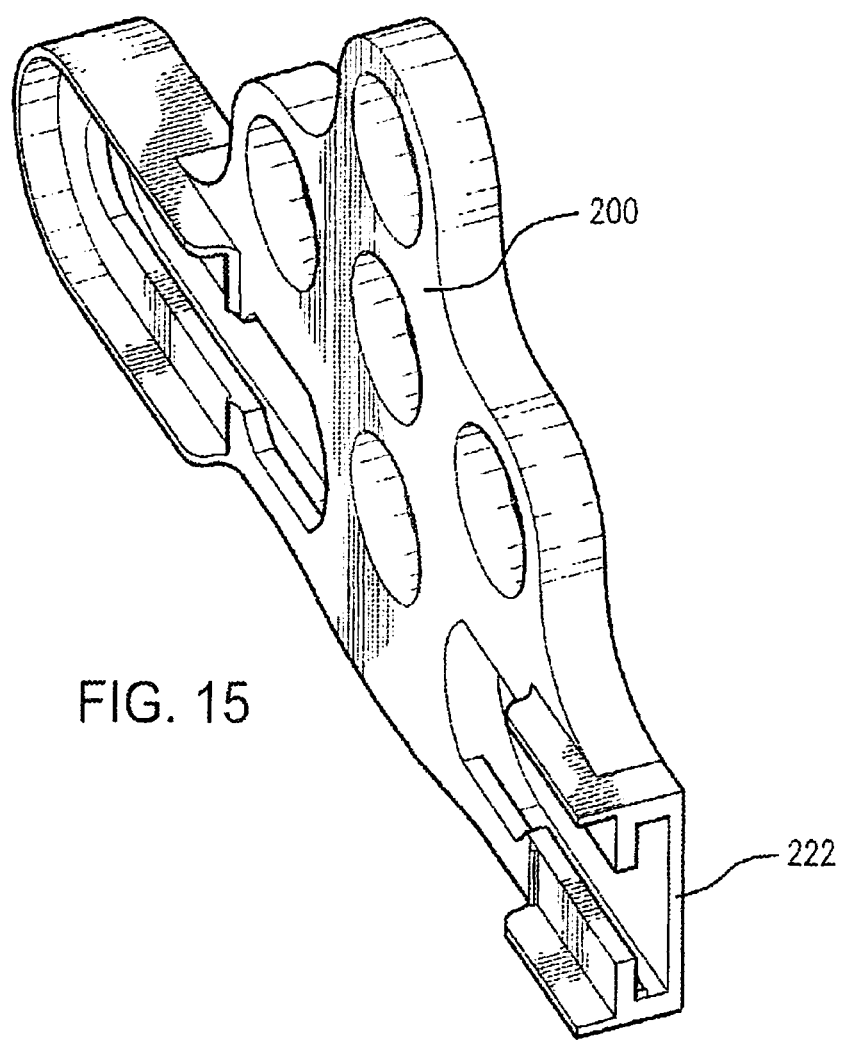
FIG. 15 is a section view of another embodiment of a plate of the fixation system.

A variety of configurations can be used for the first and second interlocking surfaces 400 and 402, respectively. For example, either or each of the first interlocking surface 400 and the second interlocking surface 402 can include a series of extending projections 404 configured for mating engagement when the housing 300 is in the second position. The extending projections 404 can be square or rounded teeth as shown, for example, in FIG. 13, radial or parallel ribs as shown in FIG. 14a, textured or knurled surfaces such as the pyramid-shaped projections, as shown in FIG. 14b, or any other suitable shape such that the first and second interlocking surfaces 400 and 402, respectively can be engaged when the housing 300 is in the second position. The second interlocking surface 402 can be on an outside edge of the flange 310 as depicted in FIG. 10, or can be on a top surface of the flange 310 as shown in FIGS. 14a and 14b, or provided on the base portion (not shown) as desired depending upon the location of the first interlocking surface 400. The first interlocking surface 400 has a mating configuration and preferably disposed to allow uninhibited movement of the adjustable housing 300 when in the first position, as depicted for example, in FIG. 11a.

In a preferred embodiment of the invention the second interlocking surface 402 includes a series of radially extending projections 404 as shown in FIG. 13. The radially extending projections 404 extend outward from the outside edge of flange 310 of the adjustable housing 300.

Alternatively, the first and second interlocking surface 402 can be configured to form a cold weld when the adjustable housing 300 is in the second position.

Figure 21:
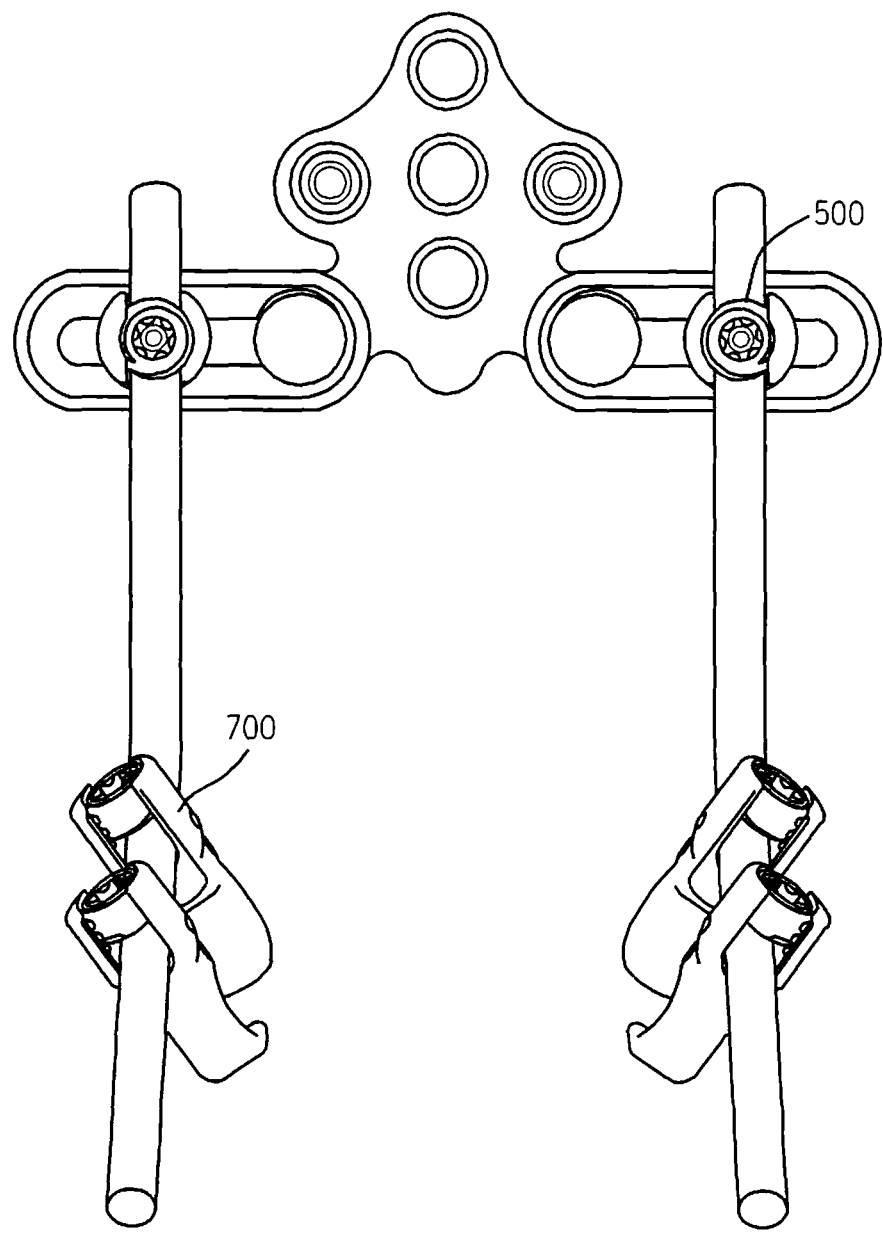
FIG. 21 is a top view of another embodiment of the fixation system.
Figure 22:
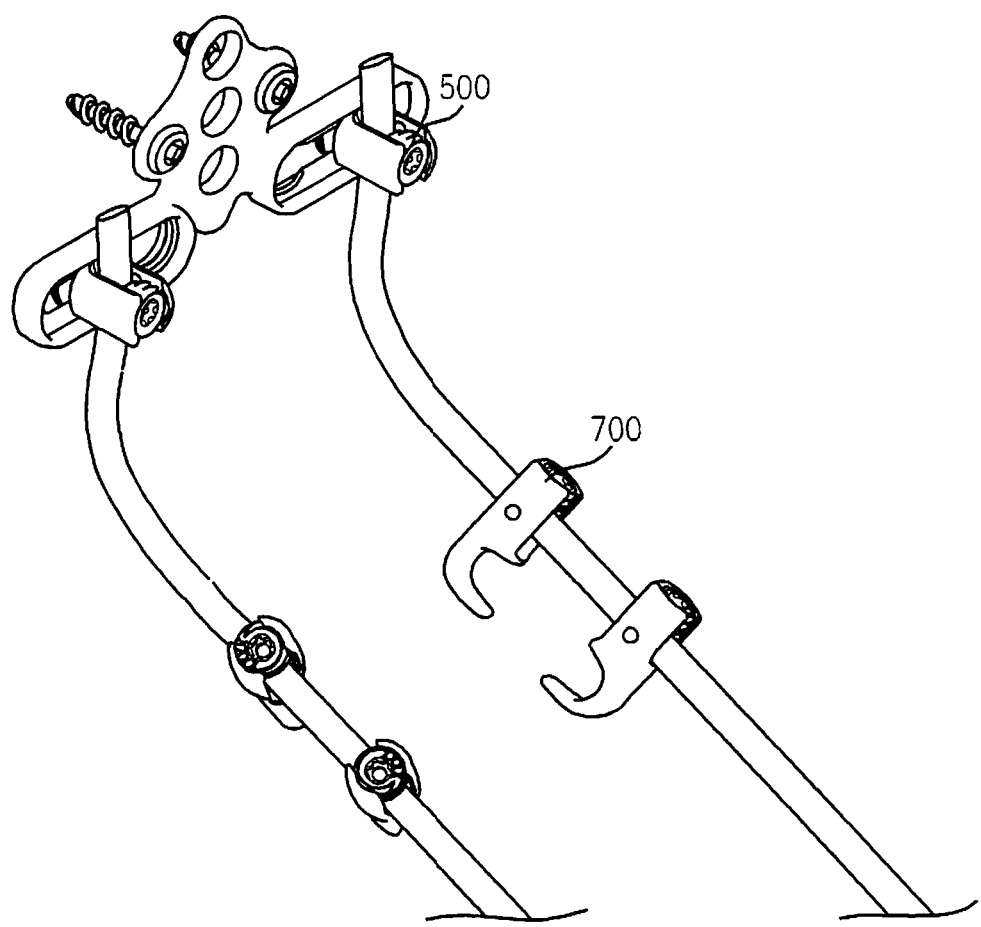
FIG. 22 is a perspective view of the fixation system.

In accordance with one aspect of the invention, the system includes a securing device 500 such as a threaded nut or set screw, as shown in FIGS. 21 and 22. In this embodiment, the body portion 302 of the adjustable housing 300 has a corresponding threaded surface 406, shown in FIG. 11a, to receive the securing device 500 and secure a spinal rod 600 within the internal cavity of the adjustable housing 300. Preferably, the adjustable housing 300 is drawn from the first position to the second position upon securing of the securing device 500. The securing device 500 can be a set screw that is received in internal threads 406 in the adjustable housing 300. Alternatively, the securing device 500 can be a nut that is received in external threads in the adjustable housing 300. Other suitable securing devices also can be used as known in the art.

Figure 23:
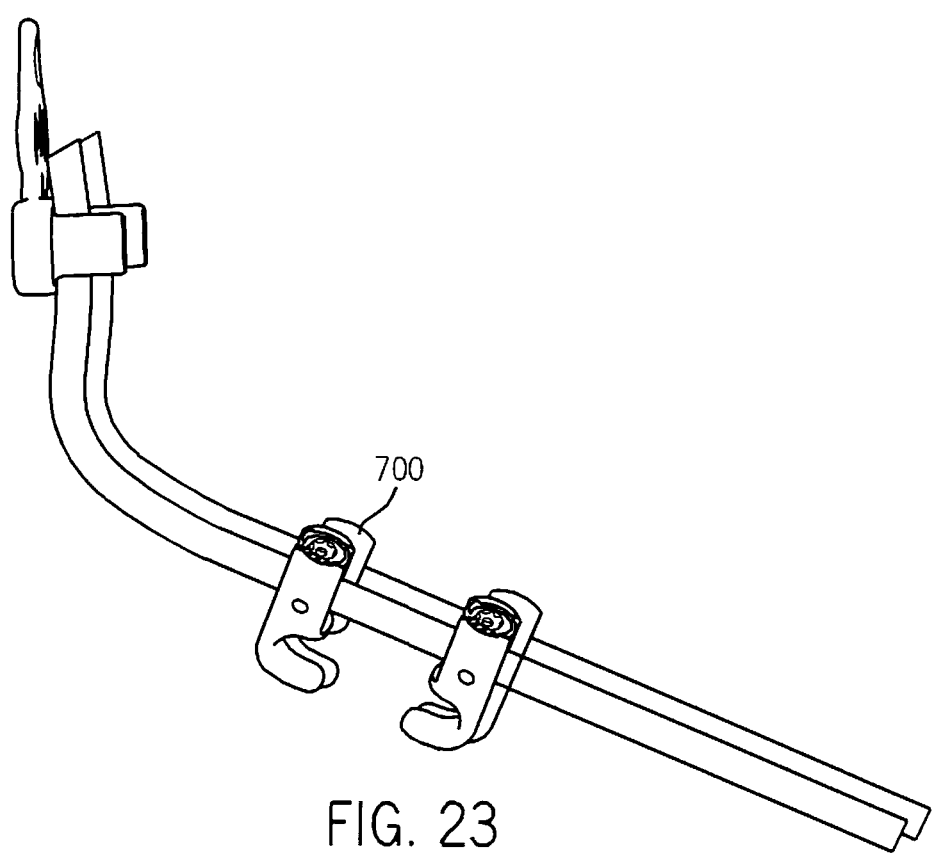
FIG. 23 is a side view of the fixation system.

The rod 600 supports and preferably immobilizes one or more levels of the spine 104 and can be of any suitable construction, many of which are known. In a preferred embodiment, as shown in the FIGS. 1 and 2, the rod 600 will be in the form of a straight, cylindrically shaped metallic rod extending along a longitudinal axis and formed of a suitable biocompatible material that can be deformed along its length as required to conform to the patient morphology. However, it should be understood that pre-bent or pre-deformed rods and/or noncylindrical rods can also be used in the system 100. The rod 600 has a proximate end portion that is adjacent the plate 200 for connection thereto, and a length extending to a distal end portion adjacent at least one of the vertebra 108. Typically, at least the distal end of the rod 600, and potentially other portions of its length, will be affixed to at least one of the vertebra 108 using a suitable anchoring system, many of which are known and which will typically include a bone screw, bolt, or hook 700 as shown in FIGS. 21-23 and some sort of rod connector that is either integral with the bone screw or otherwise connectable to the bone screw.

The components of the system 100 can be made of any material that is biocompatible for implantation. Examples of such materials include, but are not limited to, stainless steel, commercially pure titanium, titanium in its various alloys, and biocompatible polymer materials. If desired, the surface of the components can be treated to, for example, strengthen the material, alter the healing response after implantation, or modify the surface chemistry. Such surface treatments include, but are not limited to, coatings such as chrome, sintered titanium, ceramic coat, polymeric coating, coatings or materials with embedded therapeutic agents, or any other type of coating.

The system 100 according to the invention can be used in minimally invasive surgery (MIS) procedures or in non-MIS procedures, as desired, and as persons of ordinary skill in the art who have the benefit of the description of the invention understand. MIS procedures seek to reduce cutting, bleeding, and tissue damage or disturbance associated with implanting a spinal implant in a patient's body. Exemplary procedures can use a percutaneous technique for implanting longitudinal rods and coupling elements. Examples of MIS procedures and related apparatus are provided in U.S. patent application Ser. No. 10/698,049, filed Oct. 30, 2003, U.S. patent application Ser. No. 10/698,010, filed Oct. 30, 2003, and U.S. patent application Ser. No. 10/697,793, filed Oct. 30, 2003, incorporated herein by reference.

Persons skilled in the art can make various changes in the shape, size, number, and/or arrangement of parts without departing from the scope of the invention as described herein. In this regard, it should also be appreciated that the various relative dimensions of each of the components are shown in the figures for purposes of illustration only and can be changed as required to render the system 100 suitable for its intended purpose.

Various other modifications and alternative embodiments of the invention in addition to those described herein will be apparent to persons of ordinary skill in the art who have the benefit of the description of the invention. Accordingly, the description, including the appended drawings, is to be construed as illustrative only, with the understanding that preferred embodiments are shown.

The invention claimed is:

1. A system for fixing a region of a skull to a portion of a spine, the system comprising:

a plate configured to contact the region of the skull and be secured thereto, the plate having a top surface and at least one elongated slot defined therein, the at least one elongated slot having a transverse dimension and the plate having a threaded opening in communication with the at least one elongated slot, the threaded opening having a diameter greater than the transverse dimension; and an adjustable housing having a body portion and a base portion, the body portion having a channel defined therein to receive a spinal rod, the base portion having a first portion extending from the body portion with a first cross dimension that is less than the transverse dimension, the base portion further including a threaded portion with a threaded exterior surface sized to mate with the threaded opening; and the adjustable housing configured to be received in the threaded opening in a first direction and movable into and along the elongated slot in a second direction after the threaded exterior surface is fully threaded through the threaded opening of the plate, wherein the first direction and the second direction are two different directions, wherein the transverse dimension is orthogonal to the first direction; and the channel of the body portion of the adjustable housing is generally U-shaped, the channel open on an end of the body portion opposite the base portion and open on opposing lateral sides of the body portion, the channel of the body portion is structured to be capable of receiving the spinal rod with the spinal rod extending out of the channel on the opposing lateral sides of the body portion.

2. The system of claim 1, wherein the plate includes a recessed surface along at least a portion of the elongated slot opposite the top surface.

3. The system of claim 1, further comprising a securing device, the body portion of the adjustable housing having a threaded surface to receive the securing device and secure the spinal rod within the channel, and further wherein the adjustable housing is drawn from a first position in which the adjustable housing is slideably received in the elongated slot to a second position in which the adjustable housing is locked in position in the elongated slot upon receipt of the securing device.

4. The system of claim 1, wherein the plate further includes at least one opening to receive a fastener therethrough to secure the plate to the skull.

5. The system of claim 1, wherein the at least one elongated slot comprises two elongated slots.

6. The system of claim 5, wherein the plate has a threaded opening in communication with an end of each elongated slot.

7. A method for fixing a region of a skull to a portion of a spine, the method comprising:

securing a plate to the region of the skull, the plate having a top surface and at least one elongated slot defined therein, the at least one elongated slot having a transverse dimension and the plate having a threaded opening in communication with the at least one elongated slot, the threaded opening having a diameter greater than the transverse dimension;

fully threading a threaded portion of an adjustable housing through a respective threaded opening of one of said at least one elongated slot in a first direction, the adjustable housing having a body portion and a base portion, the body portion having a channel defined therein to receive a spinal rod, the base portion having a first portion extending from the body portion with a first cross dimension that is less than the transverse dimension, the adjustable housing further including the threaded portion extending from the first portion with a threaded exterior surface, the threaded exterior surface sized to mate with the threaded opening; and moving the adjustable housing into and along the elongated slot in a second direction to position the adjustable housing in the elongated slot, wherein the first direction and the second direction are two different directions, wherein the transverse dimension is orthogonal to the first direction.

8. The method of claim 7, wherein the plate includes a recessed surface along at least a portion of the elongated slot opposite the top surface.

9. The method of claim 7, further comprising securing the spinal rod within the channel of the adjustable housing, wherein the body portion of the adjustable housing has a threaded surface to receive a securing device to secure the spinal rod within the channel, and further wherein the adjustable housing is drawn from a first position in which the adjustable housing is slideably received in the elongated slot to a second position in which the adjustable housing is locked in position in the elongated slot upon receipt of the securing device.

10. The method of claim 7, wherein the plate further includes at least one opening to receive a fastener therethrough to secure the plate to the skull.

11. The method of claim 7, wherein the at least one elongated slot comprises two elongated slots.

12. The method of claim 11, wherein the plate has a threaded opening in communication with an end of each elongated slot.

13. A system for fixing a region of a skull to a portion of a spine, the system comprising:

a plate configured to contact the region of the skull and be secured thereto, the plate having a top surface and at least one elongated slot defined therein, the at least one elongated slot having a transverse dimension and the plate having a threaded opening in communication with the at least one elongated slot, the threaded opening having a diameter greater than the transverse dimension;

an adjustable housing having a body portion and a base portion, the body portion having a channel defined therein to receive a spinal rod, the base portion having a first portion extending from the body portion with a first cross dimension that is less than the transverse dimension, the base portion further including a threaded portion with a threaded exterior surface sized to mate with the threaded opening;

a securing device, the body portion of the adjustable housing having a threaded surface to receive the securing device and secure the spinal rod within the channel, wherein the adjustable housing is configured to be received in the threaded opening in a first direction and movable into and along the elongated slot in a second direction after the threaded exterior surface is fully threaded through the threaded opening of the plate, wherein the first direction and the second direction are two different directions, wherein the transverse dimension is orthogonal to the first direction.

14. The system of claim 13, further wherein the adjustable housing is drawn from a first position in which the adjustable housing is slideably received in the elongated slot to a second position in which the adjustable housing is locked in position in the elongated slot upon receipt of the securing device.

* * * * *